United States Patent
Rinck et al.

(10) Patent No.: US 12,229,333 B2
(45) Date of Patent: Feb. 18, 2025

(54) TECHNIQUE FOR VISUALIZING INTERACTIONS WITH A TECHNICAL DEVICE IN AN XR SCENE

(71) Applicant: Siemens Healthineers AG, Forchheim (DE)

(72) Inventors: Daniel Rinck, Forchheim (DE); Aniol Serra Juhe, Nuremberg (DE)

(73) Assignee: SIEMENS HEALTHINEERS AG, Forchheim (DE)

(*) Notice: Subject to any disclaimer, the term of this patent is extended or adjusted under 35 U.S.C. 154(b) by 0 days.

(21) Appl. No.: 18/499,770

(22) Filed: Nov. 1, 2023

(65) Prior Publication Data
US 2024/0143069 A1 May 2, 2024

(30) Foreign Application Priority Data
Nov. 2, 2022 (EP) .................................... 22205125

(51) Int. Cl.
*G06F 3/01* (2006.01)
*G06F 3/03* (2006.01)

(52) U.S. Cl.
CPC ............ *G06F 3/011* (2013.01); *G06F 3/0304* (2013.01)

(58) Field of Classification Search
CPC ........ G06F 3/011; G06F 3/0304; G06F 3/016; A61B 34/10
USPC ......................................................... 348/47
See application file for complete search history.

(56) References Cited

U.S. PATENT DOCUMENTS

| 11,250,637 | B1 | 2/2022 | Tan et al. |
| 2016/0191887 | A1* | 6/2016 | Casas ...................... A61B 34/10 348/47 |
| 2018/0232052 | A1* | 8/2018 | Chizeck .................. G06F 3/016 |
| 2019/0380792 | A1 | 12/2019 | Poltaretskyi et al. |
| 2020/0275976 | A1 | 9/2020 | McKinnon et al. |
| 2022/0265357 | A1 | 8/2022 | Morvan et al. |

FOREIGN PATENT DOCUMENTS

| WO | WO 2020163358 A1 | 8/2020 |
| WO | WO 2021016429 A1 | 1/2021 |

OTHER PUBLICATIONS

"NVIDIA Isaac ROS", in: https://developer.nvidia.com/isaac-ros [abgerufen am Oct. 18, 2023];.

(Continued)

*Primary Examiner* — Abdul-Samad A Adediran
(74) *Attorney, Agent, or Firm* — Harness, Dickey & Pierce, P.L.C.

(57) ABSTRACT

A computer-implemented method for visualizing interactions in an extended reality (XR) scene, the computer-implemented method comprising: receiving a first dataset representing an XR scene including a technical device; displaying the XR scene on an XR headset or a head-mounted display (HMD); providing a room for a user wearing the XR headset or HMD for interacting with the XR scene, wherein the room includes a set of optical sensors including at least one optical sensor at a fixed location relative to the room; detecting optical sensor data of the user as a second dataset while the user is interacting with the XR scene in the room; and fusing the first dataset and the second dataset to generate a third dataset.

19 Claims, 12 Drawing Sheets

(56) References Cited

OTHER PUBLICATIONS

Luc, Pauline et al.: "Predicting Deeper into the Future of Semantic Segmentation." ICCV2017-International Conference on Computer Vision, Oct. 2017, Venise, Italy, pp. 648-657, 10.1109/ICCV.2017. 77. hal-01494296v2;.
Gu, Jinwei, et al. "Dynamic facial analysis: From bayesian filtering to recurrent neural network." Proceedings of the IEEE conference on computer vision and pattern recognition. 2017.;.
Babu, Sudharshan Chandra: "A 2019 guide to Human Pose Estimation with Deep Learning", Apr. 12, 2019, in: https://nanonets.com/blog/human-pose-estimation-2d-guide/ [abgerufen am Oct. 18, 2023];.
PUN "The Ease-of-use of Unity's Networking with the Performance & Reliability of Photon Realtime", Download Dec. 8, 2022 https://www.photonengine.com/pun;.
Video "Holoportation" https://www.youtube.com/watch?v=7d5906cfaMO Date of Download: Aug. 26, 2022;.
Chen, Liang-Chieh, et al. "Deeplab: Semantic image segmentation with deep convolutional nets, atrous convolution, and fully connected crfs." IEEE transactions on pattern analysis and machine intelligence 40.4 (2017): 834-848.;.
Newcombe, R. A. et al: "KinectFusion: Real-time dense surface mapping and tracking", Mixed and Augmented Reality (ISMAR), 2011 10th IEEE International Symposium on, IEEE, Oct. 26, 2011 (Oct. 26, 2011), pp. 127-136, XP032114483; 2011;.
Pfister, Tomas et al. "Flowing convnets for human pose estimation in videos." Proceedings of the IEEE international conference on computer vision. 2015.;.
Nie Y. et al.: "Rfd-net: Point scene understanding by semantic instance reconstruction", pp. 4606-4616 (Jun. 2021), https://doi.org/10.1109/CVPR46437.2021;.
Microsoft Mesh https://www.microsoft.com/en-us/mesh;.
He, Kaiming, et al. "Mask r-cnn." Proceedings of the IEEE international conference on computer vision. 2017.;.
Wang, Limin et al. "Action recognition with trajectory-pooled deep-convolutional descriptors." Proceedings of the IEEE conference on computer vision and pattern recognition. 2015.;.
Tran, Du, et al. "Learning spatiotemporal features with 3d convolutional networks." Proceedings of the IEEE international conference on computer vision. 2015.;.
Microsoft Holoportation https://www.microsoft.com/en-us/research/project/holoportation-3/;.
Kubach, B. "Microsoft erklärt: Was ist Microsoft Mesh? Definition & Funktionen" in: https://news.microsoft.com/de-de/microsoft-erklaert-was-ist-microsoft-mesh/ [abgerufen am Oct. 18, 2023];.
Gadde, Raghudeep et al. "Semantic video cnns through representation warping." Proceedings of the IEEE International Conference on Computer Vision. 2017.;.
"An introduction to Depthkit capture: Depthkit Core, Azure Kinect and the Refinement Algorithm", in: https://www.depthkit.tv/tutorials/azure-kinect-microsoft-volumetric-capture-depth-workflow-depthkit [abgerufen am Oct. 18, 2023];.
"NVIDIA Isaac Sim", in: https://developer.nvidia.com/isaac-sim [Oct. 18, 2023];.
"NVIDIA Omniverse Replicator for DRIVE Sim Accelerates AV Development, Improves Perception Results", in: https://blogs.nvidia.com/blog/2021/11/09/drive-sim-replicator-synthetic-data-generation/?ncid=so-yout-833884-vt03#cid=gtcnov21_so-yout_en-us [Oct. 18, 2023];.
Youtube: "Demo: The magic of AI neural TTS and holograms at Microsoft Inspire 2019", in: https://www.youtube.com/watch?v=auJJrHgG9Mc&t=1s [Oct. 30, 2023].

* cited by examiner

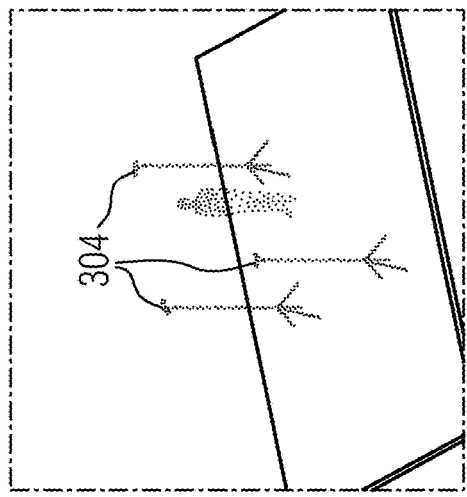
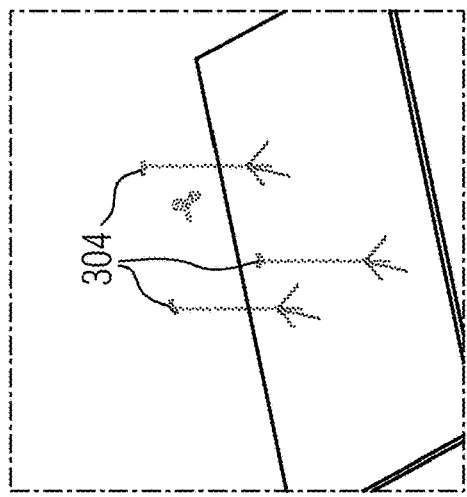
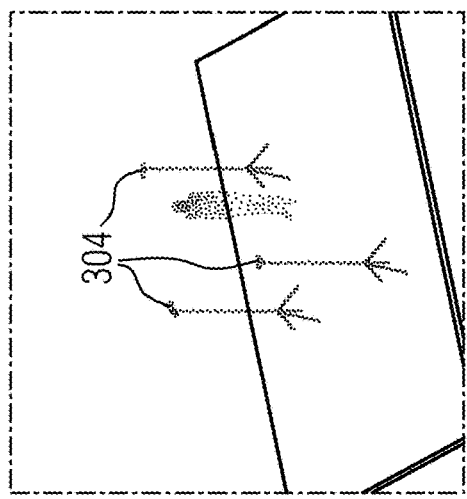
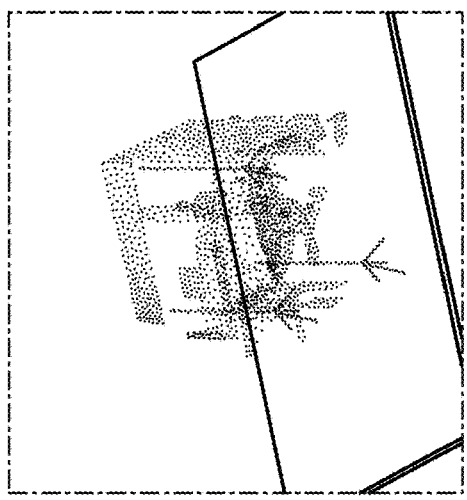

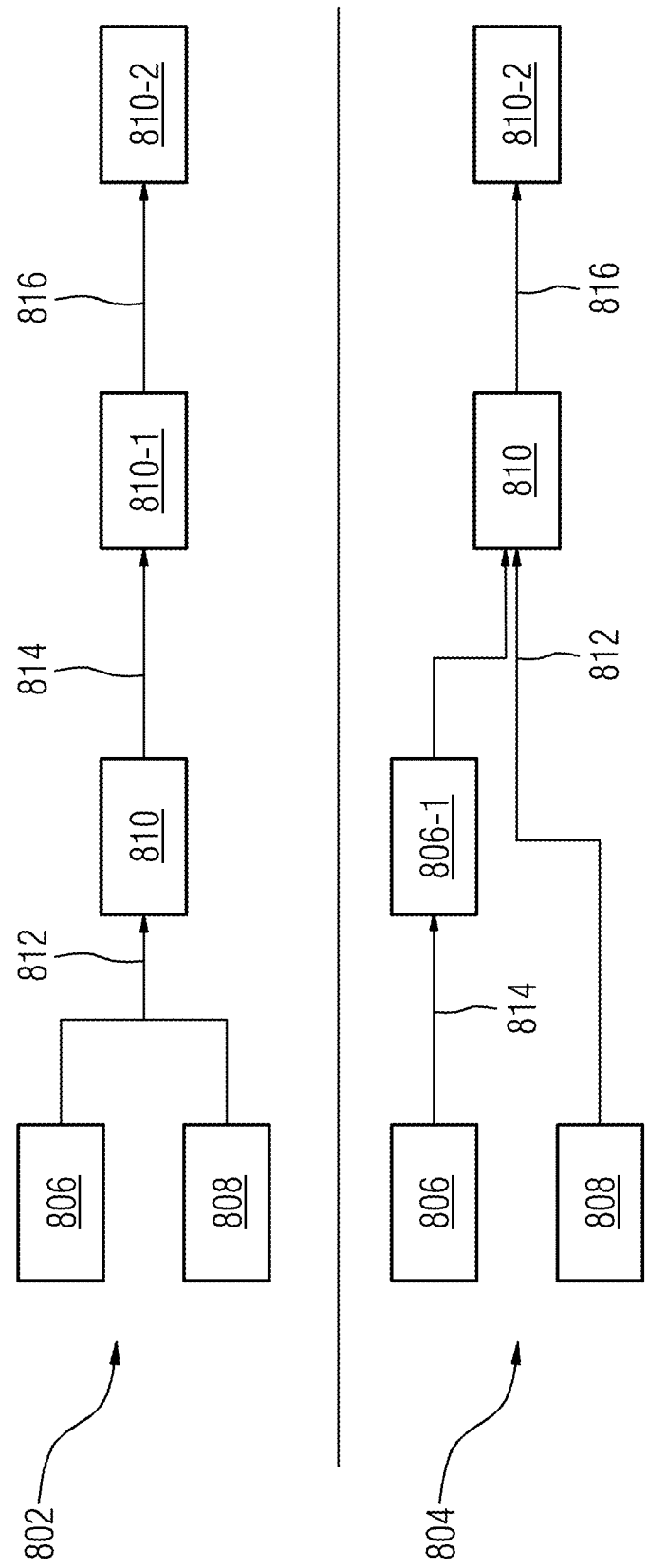

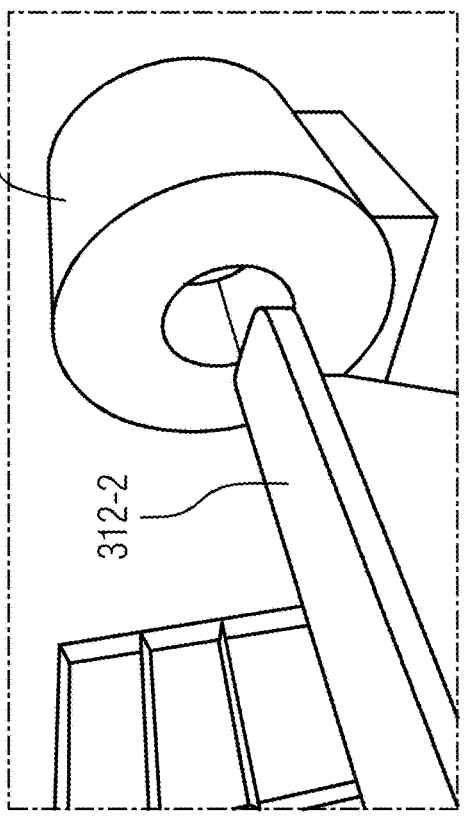
FIG 9A
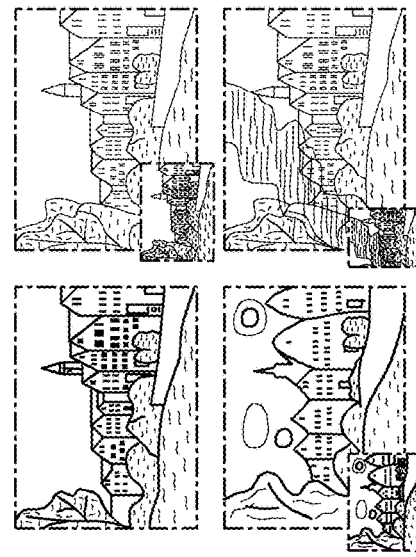
FIG 9B
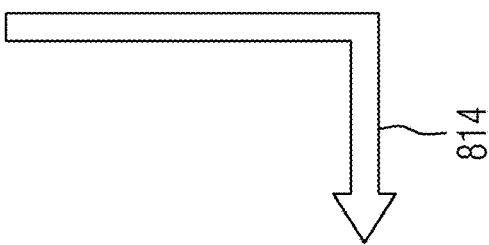
FIG 9C
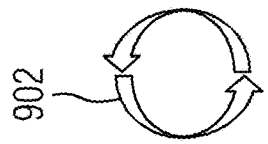
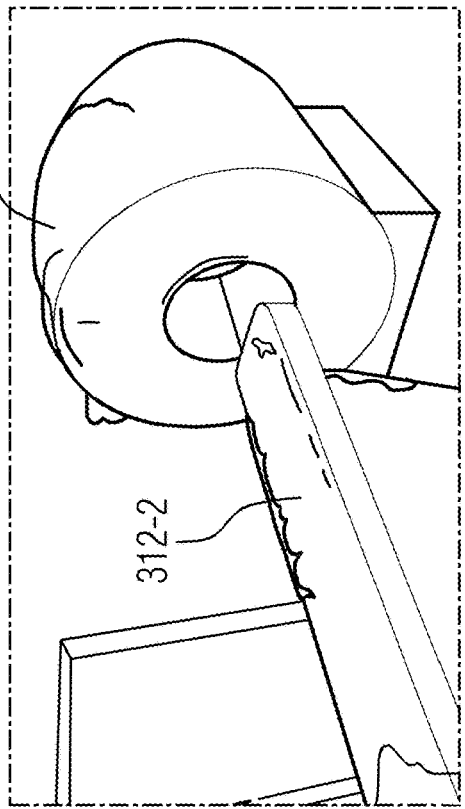
FIG 9D

TECHNIQUE FOR VISUALIZING INTERACTIONS WITH A TECHNICAL DEVICE IN AN XR SCENE

CROSS-REFERENCE TO RELATED APPLICATION(S)

The present application claims priority under 35 U.S.C. § 119 to European Patent Application No. 22205125.2, filed Nov. 2, 2022, the entire contents of which is incorporated herein by reference.

FIELD

The present disclosure relates to a technique for visualizing interactions with a technical device, in particular a medical device, in an extended reality (XR) scene. Alternatively or in addition, the present disclosure relates to providing a technique for virtual usability engineering and/or product development of the technical device, in particular using virtual usability tests. Further alternatively or in addition, the present disclosure relates to providing monitoring and training of human operators (also denoted as users) of the technical device, in particular the medical device, using a virtual device in an XR environment.

BACKGROUND

Conventional product development of technical devices, in particular of medical devices, requires the steps of understanding the (e.g., clinical) needs (also denoted as usability and/or requirement engineering), of evaluating design options of both hardware and the operating software (also denoted as design thinking), of developing early prototypes (also denoted as mock-up) in order to de-risk the development of the technical device and of further developing the technical device.

For technical devices comprising some computer-implemented control, e.g., using artificial intelligence (AI), conventional product development further comprises the steps of collecting data (e.g., of a depth camera) for scene analysis and testing, of developing an automatization (e.g., a computer algorithm, and/or training a, e.g., deep, neural network) and of applying the automatization for completing the product development.

SUMMARY

Even if a user is closely integrated into the development process (e.g., as collaboration partner) and involved in early design discussions, there is conventionally no way to experience the full system, in particular including the interaction between hardware and software, before the first real system is developed and the software is implemented (e.g., during a system test). This might not be a problem when one is developing "just another system of its kind" as successor system, with known prior system behavior, but counts in when one aims for addressing a completely new system, technical device, market segment, and/or target customer with no prior knowledge and challenging siting constraints (e.g., magnetic resonance imaging, MRI, which requires a very compact design for use in a medical office, in particular when not located in a hospital or radiology department).

Especially when developing an autonomous AI driven technical device (or system), which is for example aware of its environment, it is conventionally hard, or even impossible, to collect meaningful data early in the development process. One basically needs to wait until the first technical devices (or systems) are readily installed at a customer site in order to collect the necessary data with a dedicated customer work-in-progress package (WIP). Also, the required large amount of collected data is conventionally challenging. While training data can be augmented (e.g., by rotating, mirroring, and/or zooming existing images or generating new, synthetic images), the conventional challenge is a lack of realism of such modified and/or synthetic training data.

Conventional usability and/or requirement engineering and design thinking solutions consist in building miniature hardware wood or paper models and providing print-outs and/or sketches and (oftentimes non-functional) software protypes (e.g., based on PPT or HTML). These conventional methods suffer from a lack of interaction between hardware and software. Not only the development of a technical device is thereby restrained, but also human operators can only be successfully trained (e.g., for an inference and/or application phase) once the end product has been deployed and sufficient training data have been accumulated, leading to delays of using the technical device, in particular a medical device for diagnostic or therapeutic purposes, after the hardware product has been produced.

It is therefore an object of one or more example embodiments of the present invention to provide a technique for improving detection of errors and weaknesses in the design of a technical device, in particular a medical device, as early as possible. Alternatively or in addition, it is an object of one or more example embodiments of the present invention to enable monitoring, controlling, analysing, and/or training of human operator interactions with the technical device as early as possible and/or before deployment of the physical end product technical device.

At least this object is solved by a method for visualizing interactions in an extended reality (XR) scene, by a computing device, by a system, and by a computer program product according to the appended independent claims. Advantageous aspects, features and embodiments are described in the dependent claims and in the following description together with advantages.

In the following, a solution according to embodiments of the present invention is described with respect to the claimed method as well as with respect to the claimed computing device and system. Features, advantages, and/or alternative embodiments herein can be assigned to the other claimed objects (e.g., the computer program or a computer program product) and vice versa. In other words, claims for the computing device and/or the system can be improved with features described or claimed in the context of the method. In this case, the functional features of the method are embodied by structural units of the system and vice versa, respectively.

As to a method aspect, a computer-implemented method for visualizing interactions in an extended reality (XR) scene is provided. The method comprises a step of receiving a first dataset. The first dataset represents an XR scene comprising at least a technical device (e.g., a medical device, in particular a medical imaging device). The method further comprises as step of displaying the received XR scene on an XR headset or a head-mounted display (HMD). The method further comprises as step of providing a room for a user (also denoted as human operator, or shortly operator). The user wears the XR headset or HMD for interacting with the XR scene. The XR scene is displayed on the XR headset or HMD. The room comprises a set of optical sensors. The set of optical sensors comprises at least one optical sensor at a fixed (and/or predetermined) location relative to the room (e.g., at some edge or corner). The method further comprises a step of detecting, via the set of optical sensors, optical sensor data of the user as a second dataset. The optical sensor data are detected while the user is interacting in the room with the XR scene and the XR scene is displayed on the XR headset or HMD. The method still further comprises a step of fusing the first dataset and the second dataset for generating a third dataset.

The method may further comprise a step of providing the third dataset. Alternatively or in addition, the method may further comprise a step of rendering the, e.g., provided, third dataset. The third dataset may be rendered on a further XR headset and/or HMD, and/or on any other display, e.g., comprising a screen.

The XR may alternatively be denoted as mixed reality. Alternatively or in addition, XR may comprise augmented reality (AR) and/or virtual reality (VR).

The visualizing interactions in the XR scene may comprise visualizing interactions with a virtual medical device, e.g., a device for Magnetic Resonance Imaging (MRI). The device for MRI may also be denoted as MRI scanner (or briefly MR scanner).

The first dataset may comprise a synthetically generated virtual scene of the technical device.

The technical device may comprise a medical device.

Alternatively or in addition, the technical device may comprise a medical imaging device, e.g., an MRI scanner, a device for computed tomography (CT), for positron-emission-tomography (PET), for single-photon emission computed tomography (SPECT), for radiography (also denoted as X-ray imaging), and/or for ultrasound. E.g., the MRI scanner may be configured for dental applications and/or imaging of at least part of the jawbones of a patient.

Alternatively or in addition, the technical device my comprise an examination table (also denoted as patient table or patient bench), equipment of a medical imaging device (e.g., one or more coils of an MRI scanner), a user interface (UI), in particular a graphical user interface (GUI), and/or any other control item.

The UI may comprise a button. Alternatively or in addition, the GUI may comprise a touchscreen of a tablet computer and/or of a smartphone.

The XR headset may comprise a modification, and/or an extension, of a virtual reality (VR) headset. Alternatively or in addition, the XR headset may comprise a modification, and/or an extension of a conventional XR headset, e.g., Microsoft HoloLens.

Alternatively or in addition, the HMD may comprise a virtual reality headset.

Alternatively or in addition, the HMD may comprise a small display and/or projection technology integrated into eyeglasses, mounted on a helmet, and/or mounted on a hat.

Alternatively or in addition, the HMD may comprise a head-up display (also: heads-up display; briefly: HUD). A HUD may comprise a type of HMD that does not block the user's vision, but superimposes the image on the user's view of the real world.

Alternatively or in addition, a HUD may comprise a retinal display that "paints" (and/or projects) a picture directly on the sensitive part of the user's retina. Although the image may appear to be on a screen at the user's ideal viewing distance, there need not be any (and/or it is not necessary that there is an) actual screen in front of the user, just special optics (e.g., modified eyeglasses) that reflect the image back into the eye.

Alternatively or in addition, a HUD need not be (and/or it is not necessary that a HUD is) worn by the user. Further alternatively or in addition, a HUD may be projected on a surface (e.g., on a car windshield or plane windshield).

In some embodiments, an HMD may comprise motion sensors to determine direction and/or movement (e.g., to provide context-sensitive geographic information). Alternatively or in addition, the HMD may comprise an interface, e.g. comprising motion sensors, to an immersive virtual reality application.

The XR headset, and/or the HMD, may comprise a display (which may also be denoted as screen), on which the first dataset, and/or the XR scene, is displayed.

According to some embodiments, at least two users, each having a XR headset and/or HMD, may interact with the (e.g., same) XR scene.

The at least two users may interact with the XR scene in the same room. According to some embodiments, the XR headset and/or HMD of any user may be transparent. The transparency may comprise that, along with the XR scene, any user sees all other users in the same room.

Alternatively or in addition, the XR scene displayed to a first user may comprise a representation of the second user, and vice versa. Further alternatively or in addition, the XR scene displayed to the first user may comprise the third dataset of the second user, and vice versa.

Displaying the other users (e.g., the second user being displayed to the first user, or vice versa) with the XR scene, e.g., as part of the XR scene and/or via a fusing of datasets (e.g., the first dataset representing the XR scene and one or more second datasets related to any one of the other users), allows for users being located in different rooms to interact simultaneously with the same XR scene (and/or with each other).

The room may alternatively be denoted as space, area, and/or as green screen studio.

The room may be essentially empty in the sense of having a predetermined, in particular continuous and/or flat, floor area (e.g., of rectangular shape) without any obstacles, which may obstruct a free movement of the user. E.g., an obstacle may comprise any piece of furniture (for example a table, chairs, and/or a floor lamp) or low hanging overhead lamp. Low hanging herein may denote a bottom of the overhead lamp being located lower than a height of the user (e.g., the height including any shoes, clothing and/or hairstyle).

Alternatively or in addition, the room even may comprise one or more (e.g., physical and/or mock) parts of the technical device, in particular of the medical device. E.g., the room may comprise a (e.g., wooden) model of a patient table of a (e.g., otherwise virtual) medical device (e.g., a medical imaging device such as an MRI scanner).

Further alternatively or in addition, the room may be (e.g., at least partially) furnished. E.g., the room may comprise one or more patient chairs, a patient table, and/or one or more (e.g., physical and/or mock) parts of the technical device, in particular of the medical device.

The set of optical sensors comprises at least one optical sensor. The at least one optical sensor is installed at a fixed (and/or predetermined) location within the room.

The location of the at least one optical sensor may be fixed (and/or predetermined) for a predetermined time. Alternatively or in addition, the location of the at least one optical sensor may be fixed (and/or predetermined) for (e.g., repeatedly and/or continuously) performing the method for the at least one technical device (e.g., a medical device) and/or for at least one user, e.g., until an end of (e.g., repeatedly and/or continuously) performing the method. Further alternatively or in addition, the location of the at least one optical sensor may be fixed (and/or predetermined) for (e.g., repeatedly and/or continuously) performing the method until a predetermined amount of data (e.g., comprising third datasets) has been collected.

For example, the method may be initiated with a registration procedure for being able to faithfully fuse the optical sensor data (and/or the second dataset) with the XR scene data (and/or the first dataset). During the registration procedure and the subsequent (e.g., repeatedly and/or continuously) performing of the method, the location of the at least one sensor may be fixed (and/or predetermined). After performing the method (e.g., repeatedly and/or continuously) for the at least one technical device, and/or at least one user, the method may be stopped or interrupted. The locations of one or more optical sensors may be changed to one or more other fixed (and/or predetermined locations), the registration procedure may be repeated, and the method may be, e.g., repeatedly and/or continuously) performed, e.g., for at least one other technical device, and/or at least one other user.

Alternatively or in addition, the method may be repeated with different locations of one or more optical sensors with the same at least one technical device and the same user.

The at least one optical sensor may comprise at least one camera. The camera may comprise a red-green-blue (RGB) camera, a depth camera, and/or an RGB depth (RGB-D; also: RGBD) camera.

Preferably, the set of optical sensors may comprise at least two RGB-D cameras, in particular three or four RGB-D cameras.

The optical sensors, e.g., comprising depth cameras (in particular RGB-D cameras), may be placed at different (e.g., comprising opposite) edges and/or corners of the, in particular essentially empty, room. By placing the optical sensors at different edges and/or corners of the room, an accurate, and/or faithful, image may be taken of any movement of the user, e.g., which may be blocked towards at least one side of the user by his/her body.

By detecting the optical sensor data of at least two optical sensors, in particular each comprising a depth camera (and/or more particularly an RGB-D camera), any interaction of the user with the XR scene may be correctly, and/or faithfully, located.

Alternatively or in addition, the set of optical sensors may comprise an eye-tracking sensor and/or a motion sensor, e.g., comprised in the XR headset or the HMD.

The interaction of the user with the XR scene may comprise pushing a button of the XR scene, and/or providing an input of a (in particular graphical) user interface (UI, in particular a GUI) of the XR scene, e.g., on a touchscreen.

Alternatively or in addition, the interaction of the user with the XR scene may comprise any, in particular mechanical, manipulation of the technical device. The manipulation of the technical device may comprise an input on an input interface of the technical device. The input interface may comprise a button, a UI (in particular a GUI), a mouse, a keyboard, a touchscreen, a trackpad and/or a joystick. Alternatively or in addition the manipulation may comprise relocating and/or rearranging equipment of the technical device, e.g., comprising one or more coils of an MRI scanner.

The second dataset may comprise the interactions of the user, and/or movements of the user.

The third dataset may provide the combination of the XR scene with the interactions of the user.

The third dataset may, e.g., be displayed. By displaying the third dataset, a person different from the user of the XR headset, or of the HMD, may control the user interactions, e.g., in view of the user correctly operating the technical device.

By the method, the user of the XR headset, and/or of the HMD, may be trained for operating the technical device. Thereby, a safety and/or competence of using a real version of the technical device may be improved. Thereby, the real version of the technical device may be operated efficiently from the start (and/or from deployment at its operating site).

Alternatively or in addition, by the person different from the user of the XR headset or the HMD controlling the user interactions, a training, and thereby a safety of operating the real version of the technical device, may be further improved.

Further alternatively or in addition, by the person different from the user of the XR headset, and/or of the HMD, and/or by a computer algorithm analyzing the user interactions, the technical device may be improved. E.g., deficiencies in the technical design for operating the technical device may be detected in the XR scene. A re-design eliminating, and/or mitigating, the technical design deficiencies may be performed.

The first dataset may comprise a point cloud. Alternatively or in addition, the second dataset may comprise a point cloud. Further alternatively or in addition, the third dataset may comprise a fusion of the point clouds of the first dataset and of the second dataset. Still further alternatively or in addition, the third dataset may comprise a point cloud.

By the method, the fields on computer generated images (CGI), and/or visualization, and of computer vision, e.g., comprising a scene understanding segmentation, may be combined. Alternatively or in addition, virtual usability laboratory, and/or a workflow representation at real time, may be enabled.

Any one of the first, second, and/or third, datasets may comprise a five-dimensional (5D) dataset. The 5D dataset may refer to three spatial directions (e.g., denoted as x, y, z), time and color.

The set of optical sensors may comprise at least one camera, in particular a depth camera for providing point cloud data, and more particularly an RGB-D camera.

Any one of the optical sensors may be configured to provide distance data. Alternatively or in addition, the at least one optical sensor may be extended with an ultrasonic sensor, e.g., for providing distance data.

The first dataset, the second dataset, and/or the third dataset may comprise a point cloud. Optionally, the third dataset may comprise a fusion of the point clouds of the first dataset and of the second dataset.

The third dataset may be represented as an image dataset, which may be provided, output, processed and/or rendered.

The output of the third dataset may comprise displaying the third dataset for control of the user interactions with the technical device (e.g., the medical device). Thereby, the safety of the user interaction may be improved, e.g., by visual inspection by a human supervisor, and/or human operator.

Alternatively or in addition, the processing may comprise a control algorithm, performed by a computing device, for controlling, and/or for monitoring, user interactions, e.g., in view of correctly operating the at least one technical device in the XR scene.

The third dataset may be used for providing real-time instructions. Alternatively or in addition, the third dataset may be used for generating real-time instructions which may be provided to the user.

By the real-time instructions, the user may be trained to correctly use the technical device. Thereby, the safety and the competence of operating a real version of the technical device may be improved.

The instructions may be step-by-step. Alternatively or in addition, the instructions may comprise a sequence of, in particular different, instructions.

The instructions may be provided by a computer, e.g., storing a list of instructions per application of the technical device (e.g., in terms of a digital user manual). Alternatively or in addition, the instructions may be provided by a neural network. The neural network may process the detected optical sensor data in real time for correcting and/or adjusting (e.g., a sequence of) instructions, in particular per chosen application.

An application may, e.g., comprise a predetermined examination of a patient using a medical (in particular imaging) device as the technical device. The instructions may, e.g., comprise applying one or more coils at an anatomical position of the patient to be examined, and starting an MRI scan.

The neural network may, e.g., comprise a generative adversarial network (GAN), in particular a CycleGAN. Alternatively or in addition, the neural network may be trained via the third dataset.

A trained neural network may be used to provide output data for input data. The input data comprise the third dataset and the output data may represent a semantic context of the detected optical sensor data of the interacting user.

The semantic context may also be denoted as semantic meaning. The semantic context may comprise assigning a user interaction to the technical device of the XR scene based on the detected optical sensor data.

The trained neural network may comprise a reconstruction-from-detection (RfD) neural network (shortly: also RfD-Net), e.g., as described in, or in extension of the RfD-Net of, Nie, Y., Hou, J., Han, X., Niesner, M. "Rfd-net: Point scene understanding by semantic instance reconstruction", Pp. 4606-4616 (June 2021), https://doi.org/10.1109/CVPR46437.2021, which is included herein in its entirety by reference.

The RfD-Net may provide a point scene understanding by semantic instance reconstruction.

The RfD-Net may comprise an input layer configured for receiving a point cloud of the third dataset.

The RfD-Net may further comprise a three-dimensional (3D) proposal network backbone that is configured to propose objects, in particular with Dp-dimensional features, that are decoded into Db-dimensional box parameters. The RfD-Net may further comprise a top rank dropout layer, which is configured to reserve proposals with higher objectness in the, e.g., sparse, point cloud. The reserved proposals may be comprised in, or may form, a subset of proposals. The subset of proposals may be used to independently group and/or align one or more neighboring point clouds into a cluster.

The RfD-Net may further comprise a skip propagation encoder to extend proposal features. Alternatively or in addition, the RfD-Net may further comprise a shape decoder to decode spatial occupancy values.

Alternatively or in addition, the RfD-Net may comprise a 3D detector, a spatial transformer, and/or a shape generator, in particular as hidden layers.

At an output layer of the RfD-Net, an instance mesh may be obtained.

For further details on a possible RfD-Net architecture, it is referred to the preprint arXiv:2011.14744v1, which is incorporated herein by reference.

The neural network, e.g., the RfD-Net, may be trained by providing input data in the form of the third dataset. The input data may be labeled with content data. The content data may be representing a semantic context of the user interaction.

The third dataset may also be denoted as fused image.

The semantic context may comprise assigning, and/or relating, a user interaction according to the detected optical sensor data as the second data set to (e.g., a component of) the technical device comprised in the first data set.

A first third dataset (and/or a first fusion of a first dataset and a second dataset) may, e.g., comprise that the user operated a button for moving an examination table. Alternatively or in addition, a second third dataset (and/or a second fusion of a first dataset and a second dataset) may comprise that the user applied one or more coils to a patient, e.g., on the examination table.

The third dataset may be pre-processed before it is used as input data for the trained neural network, e.g., the RfD-Net. The pre-processing may comprise an application of an image-to-image transfer learning algorithm to the third dataset.

Alternatively or in addition, the first dataset may be pre-processed before the fusion with the second dataset. The pre-processing may comprise an application of an image-to-image transfer learning algorithm to the first dataset. Generating the third dataset may comprise fusing the pre-processed first dataset and the second dataset.

The image-to-image transfer may comprise generating a synthetic dataset of an image with a predetermined translation. Alternatively or in addition, the image-to-image transfer may be performed by a CycleGAN (with GAN short for generative adversarial network). The CycleGAN may use a GAN architecture using unpaired collections of images from two different domains, in particular comprising the first dataset in a first domain and the second dataset in a second domain.

A GAN may comprise a generator and a discriminator. Alternatively or in addition, a CycleGAN may comprise two generators and two discriminators, e.g., which may be simultaneously trained.

The first dataset and/or the XR scene may be comprised in the first domain. Alternatively or in addition, the second dataset and/or the optical sensor data may be comprised in the second domain.

The first dataset need not have the (e.g., exact or realistic) properties of (or need not be) a depth camera image and/or a three-dimensional (3D) camera image (e.g., an RGB-D camera image). Alternatively or in addition, the first dataset may comprise a virtual model of the technical device. The first dataset, e.g., may be more coarsely grained than a conventional camera image, and/or, e.g., lighting effects (in particular shadows) need not be incorporated, or at least not in a natural (and/or realistic) looking way (and/or not resembling an image taken by a depth camera and/or a 3D camera, in particular an RGB-D camera).

The neural network, e.g., the RfD-Net, may be trained with a plurality of (in particularly at least partially synthetically generated) third datasets. Alternatively or in addition, the neural network, e.g., the RfD-Net, may be trained with a plurality of third datasets, which do not fully correspond to a real (in particular clinical) setting, in which optical sensor data (e.g., depth camera data and/or 3D camera data, in particular RGB-D camera data) detect both the user and the technical device (e.g., a medical device, in particular a medical imaging device).

By the image-to-image transfer, e.g., using the Cycle-GAN, the first dataset and/or the third dataset are transformed for approximating, and/or converging to, a style of a real depth camera image (and/or a 3D camera image, in particular an RGB-D camera).

A third dataset, transformed by the image-to-image transfer for obtaining a more realistic dataset, may be provided as input to the neural network, e.g., the RfD-Net. E.g., the third dataset (and/or the fused dataset) may be (e.g., firstly) input to a CycleGAN, with the output of the CycleGAN comprising a modified (e.g., more realistic) version of the third dataset. The modified (e.g., more realistic) version of the third dataset may be (e.g., secondly) input into the neural network, e.g., the RfD-Net.

The modified version of the third dataset, and/or the more realistic dataset, may comprise a photorealistic image or series of photorealistic images. Alternatively or in addition, the modified version of the third dataset, and/or the more realistic dataset, may comprise a coding of distance data in terms of gray scales (also denoted as shades of gray), and/or in terms of color scales. E.g., a darker shade of gray, and/or a darker shade of a color, may indicate a distance farther away than a lighter shade of gray, and/or a lighter shade of the color. The distance data may be provided relative to an observer (also denoted as viewer or user) of the third dataset. The observer of the third dataset may differ from the user wearing the HMD or XR headset and having the interaction with the XR scene detected, and/or encoded, via the second dataset (and/or the sensor data).

Alternatively or in addition, the first dataset (e.g., before the step of fusing) may be input to a CycleGAN, with the output of the CycleGAN comprising a modified (e.g., more realistic and/or photorealistic) version of the first dataset.

Further alternatively or in addition, the CycleGAN may first receive the first dataset, and then receive the third dataset. Thereby, realism (e.g., photorealism) of the fused third dataset may be improved in two different steps.

The trained neural network, e.g., the RfD-Net, may be further configured for receiving as input data detected optical sensor data of a user interacting with a real-world scene. The real-world scene may comprise a real version of a technical device. The real version of the technical device may correspond to the technical device of the XR scene.

The fusing may be executed in a time resolved manner and/or a location resolved manner.

The third dataset may comprise points, e.g., of the point clouds, of the first dataset and of the second dataset at identical locations (also denoted as positions) and/or at identical instances in time. Alternatively or in addition, the fused dataset can be seen as a five-dimensional (5D) dataset with the dimensions: x-coordinate, y-coordinate, z-coordinate, color, and time.

The fusing may be executed by applying a calibration algorithm. The calibration algorithm may make use of at least one registration object, in particular a registration sphere, deployed in the room.

The calibration algorithm may comprise, or may correspond to, a registration algorithm.

The at least one registration object may comprise at least one real, physical object. Alternatively or in addition, the registration object may also be denoted as calibration object. The registration object may in particular comprise a sphere.

Deploying the at least one physical object, e.g., the at least one physical sphere, in the room may comprise placing, and/or situating, the at least one physical object within the room, e.g., at a predetermined (and/or fixed) registration position (also denoted as calibration position).

The calibration algorithm may use a set of registration objects. The registration objects may be provided as real physical objects in the room. Alternatively or in addition, the registration objects may be provided as displayed virtual objects in the displayed XR scene. For registration purposes, the real physical objects may be moved such as to match the displayed virtual objects in the displayed XR scene. Optionally, the set of registration objects may comprise a set of spheres, and/or the set of virtual objects may comprise a set of spheres.

The set of registration spheres may comprise at least one real physical sphere. The at least one real physical sphere may be moved from one registration location to another registration location within the, in particular essentially empty, room.

Alternatively or in addition, the set of registration spheres may correspond to a number of registration locations.

By the spherical symmetric shape of a sphere, the registration using one or more registration spheres may be particularly simple. Alternatively or in addition, overlaying simple spherical contours of the registration spheres with the displayed virtual spheres may be particularly easy. Further alternatively or in addition, a center, and/or midpoint, of any sphere (e.g., any registration sphere and/or any displayed virtual sphere) may be easily determined.

A number of registration locations may comprise at least three, in particular four, locations.

The calibration algorithm may comprise calibrating the set of optical sensors for appropriate, and/or faithful, localization. E.g., a registration sphere may be detected by more than one optical sensor. A three-dimensional localization may be determined by combining the optical sensor data from two or more optical sensors, e.g., by triangulation.

An image position (e.g., in terms of pixels of an image of any one of the optical sensors) of the registration sphere may be assigned a location within the XR scene.

Alternatively or in addition, the calibration algorithm may comprise registering the second dataset on, or relative to, the first dataset for matching (e.g., registration) locations in the real room and the (e.g., displayed) XR scene.

The matching may comprise, or may correspond to, an overlapping of the real physical object (in particular sphere) and the displayed virtual object (in particular sphere) at a location in the displayed XR scene. E.g., the user may be instructed to position the at least one registration sphere at the location of a displayed virtual sphere, e.g., according to a predetermined sequence of a plurality of displayed virtual spheres.

The set of registration spheres may comprise a first color, e.g., green. Alternatively or in addition, the displayed virtual spheres may comprise a second color, e.g., orange, which differs from the first color. The color may serve as an identification mechanism and/or means.

The method may be used for product development of the technical device and/or for controlling the use of the technical device. Controlling the use of the technical device may comprise monitoring the use of the technical device, e.g., without providing any (in particular direct) instructions to the user. Alternatively or in addition, controlling the use of the technical device may comprise issuing an alert in case of (at least a class of) wrong inputs by the user (e.g., posing a safety risk and/or health risk, particularly in case the technical device comprises a medical device used for diagnosing and/or treating a patient).

The method may be used for monitoring the correct use of the technical device, in particular the medical (e.g., imaging) device. Thereby, a safety of using the technical device may be improved. This may be particularly relevant for the health of a patient, on which a medical device is applied.

Alternatively or in addition, by the product development, a quality of the technical device (e.g., as end-product of the product development) may be improved.

In any application of the method, an efficiency and a safety of using the technical device, in particular the medical device, may be improved.

As to a device aspect, a computing device for visualizing interactions in an XR scene is provided. The computing device comprises a first input interface configured to receive a first dataset, the first dataset representing an XR scene comprising at least a technical device. The computing device further comprises a second input interface configured to receive, from a set of optical sensors, detected optical sensor data of a user as a second dataset. The optical sensor data are received from the set of optical sensors while the user is interacting with the XR scene. The XR scene is displayed to the user on a XR headset or HMD. The set of optical sensors comprises at least one optical sensor at a fixed (and/or predetermined) location relative to the room. The computing device still further comprises a computing unit configured to fuse the first dataset and the second dataset for generating a third dataset.

The computing device may further comprise an output interface configured to output, and/or provide, the third dataset.

As to a system aspect, a system for visualizing interactions in an XR scene is provided. The system comprises at least one XR headset and/or HMD. The system further comprises an XR scene generating unit (also referred to as a XR scene generating device) configured to generate a first dataset. The first dataset represents an XR scene comprising at least a technical device. The generated XR scene is to be displayed on the at least one XR headset and/or HMD. The system further comprises a set of optical sensors for detecting optical sensor data of a user as a second dataset. The set of optical sensors comprises at least one optical sensor at a fixed (and/or predetermined) location relative to a room. The optical sensor data are detectable, via the set of optical sensors, while the user is interacting in the room with the XR scene. The XR scene is displayable on any one of the at least one the XR headset and/or HMD. The system still further comprises a computing device according to the device aspect for executing a fusing algorithm. The fusing algorithm is configured for fusing the first dataset with the second dataset for generating a third dataset.

The system may further comprise the room.

The system may further comprise an output interface for providing, e.g., outputting, the third dataset.

The XR scene generating unit may be comprised in the computing device.

The at least one XR headset and/or the at least one HMD, the computing device, and/or the XR scene generating unit, may be connected via a photon unity network (PUN), e.g., according to software available at https://www.photonengine.com/pun.

By the PUN, the use of two or more XR headsets and/or HMDs for the same XR scene may be enabled simultaneously. The XR headsets and/or HMDs may be connected (e.g., only) via the PUN.

Alternatively or in addition, any one of the XR headsets and/or HMDs may display the user interactions of the other XR headsets and/or HMDs. Further alternatively or in addition, any one of the XR headsets and/or HMDs may be located in a different, in particular essentially empty, room. The XR scene on any XR headset and/or HMD may comprise the optical sensor data of any other XR headset and/or HMD, in particular except for the optical sensor data of the XR headset, and/or of the HMD, itself.

By the PUN, a simultaneous interaction of multiple users with the XR scene and with each other may be enabled, irrespective of the users being located in the same physical room. Thereby, a training of a team for operating the at least one technical device, in particular the medical device, and/or a product development may be further improved.

As to a further aspect, a computer program product comprising program elements is provided. The program elements induce a computing device to carry out the steps of the method aspect for visualizing interactions in an XR scene according to the method aspect, when the program elements are loaded into a memory of the computing device.

As to another aspect, a computer-readable medium is provided on which program elements are stored that can be read and executed by a computing device, in order to perform steps of the method for visualizing interactions in an extended reality XR scene according to the method aspect, when the program elements are executed by the computing device.

The properties, features and advantages of this invention described above, as well as the manner they are achieved, become clearer and more understandable in the light of the following description and embodiments, which will be described in more detail in the context of the drawings. This following description does not limit the present invention on the contained embodiments. Same components or parts can be labelled with the same reference signs in different figures. In general, the figures are not for scale.

It shall be understood that a preferred embodiment of the present invention can also be any combination of the dependent claims, or above embodiments with the respective independent claim.

These and other aspects of the present invention will be apparent from and elucidated with reference to the embodiments described hereinafter.

BRIEF DESCRIPTION OF THE DRAWINGS

FIGS. 7A to 7F show a process of fusing point-clouds, wherein in FIGS. 7A to 7C, virtual point-clouds from different angles of view of the XR scene are fused to obtain the first dataset, in FIGS. 7D to 7F, point-clouds from optical sensor data from different optical sensors are fused to obtain the second dataset, and in FIG. 7G the fused virtual point-cloud and the fused optical sensor data point clouds are fused to obtain the third dataset;

FIG. 8 shows to alternatives of successively applying, to the fusing of a first and a second dataset into a third dataset, firstly a CycleGAN for image-to-image transfer and secondly applying a (in particular different) neural network, e.g., an RfD-Net, for determining a semantic context;

FIGS. 9A to 9D show an example of an initially generated image of an XR scene comprising an MRI scanner with a patient table being image-to-image transformed, using a CycleGAN, to obtain a more realistic version of the XR scene.

Any reference signs in the claims should not be construed as limiting the scope.

DETAILED DESCRIPTION

Figure 1:
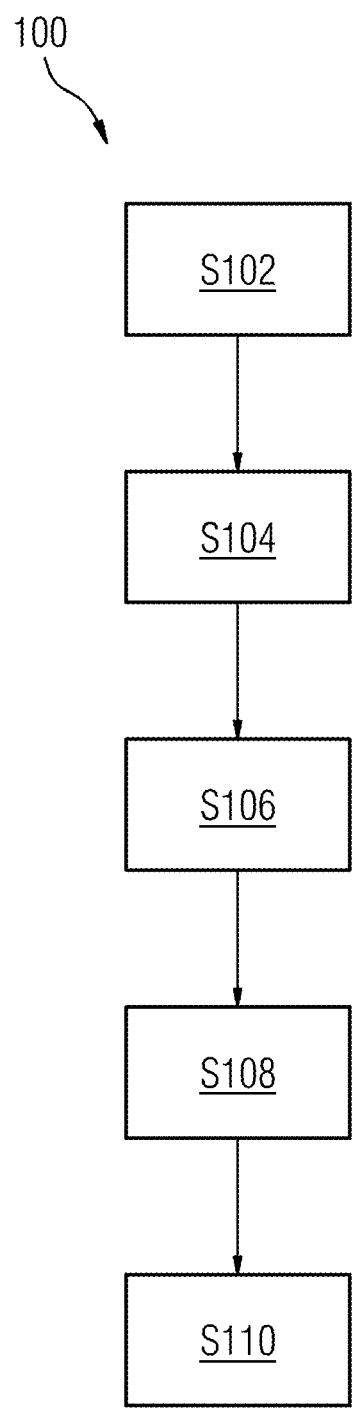
FIG. 1 is a flow chart of a computer-implemented method according to a preferred embodiment of the present invention.

FIG. 1 shows an exemplary flow chart of a computer-implemented method for visualizing interactions in an extended reality (XR) scene. The method is generally referred to reference sign 100.

The method 100 comprises a step S102 of receiving a first dataset. The first dataset represents an XR scene comprising at least a technical device. The technical device may, e.g., comprise a medical device, in particular a medical imaging device, and more particularly an MRI scanner.

The method 100 further comprises a step S104 of displaying the received S102 XR scene on an XR headset or on a head-mounted display (HMD).

The method 100 further comprises a step S106 of providing a room for a user. The user wears the XR headset or HMD for interacting with the XR scene. The XR scene is displayed on the XR headset or HMD. The room comprises a set of optical sensors. The set of optical sensors comprises at least one optical sensor at a fixed (and/or predetermined) location relative to the room, e.g., at an edge of the room. The room may be essentially empty, at least within a predetermined, e.g., rectangular, area.

The method 100 further comprises a step S108 of detecting, via the set of optical sensors, optical sensor data of the user as a second dataset. The optical sensor data (and/or the second dataset) are detected S108 while the user is interacting in the room with the XR scene. The XR scene is displayed S104 on the XR headset or HMD.

The method 100 still further comprises a step S110 of fusing the first dataset and the second dataset for generating a third dataset.

Figure 2:
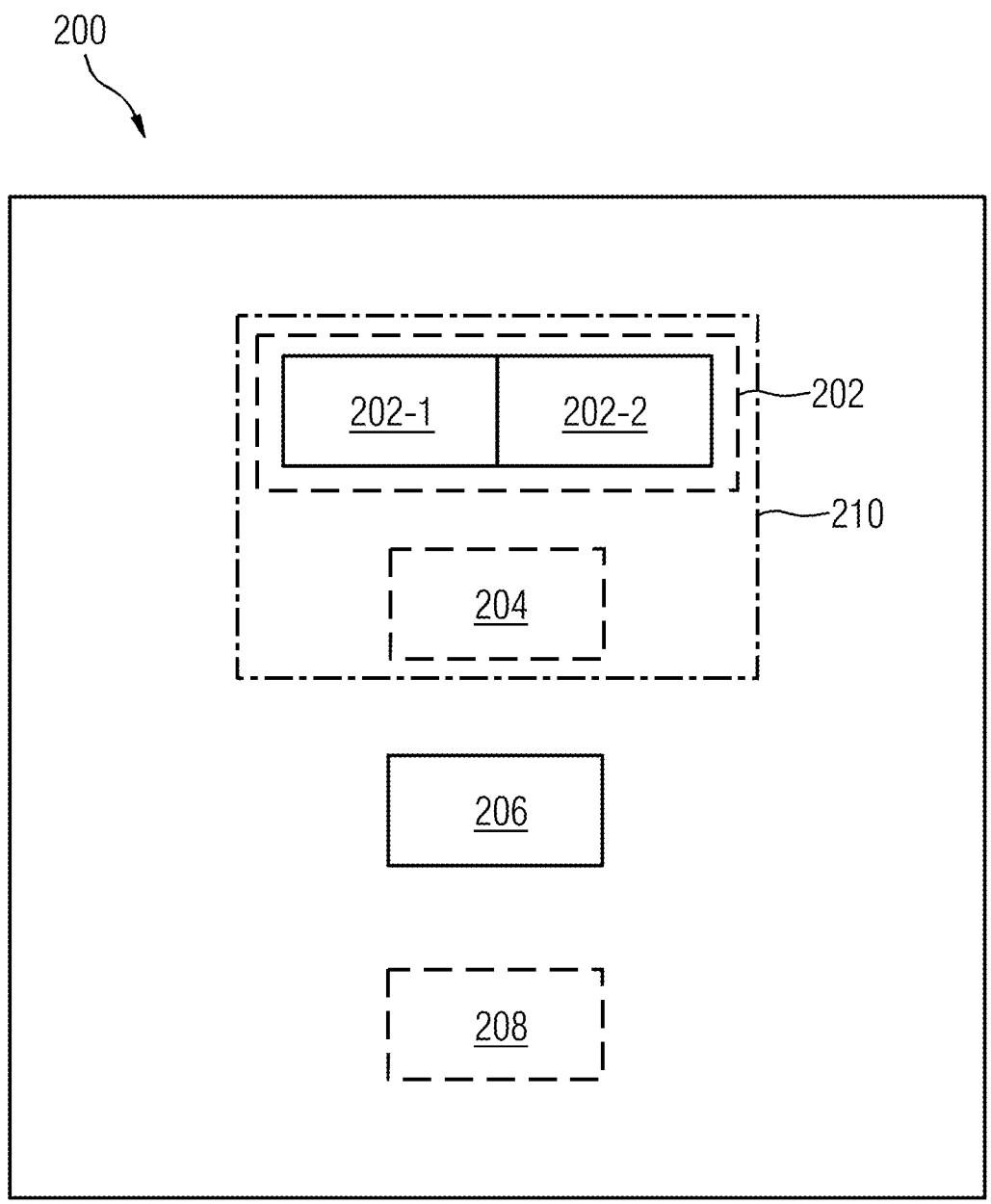
FIG. 2 is an overview of the structure and architecture of a computing device according to a preferred embodiment of the present invention.

FIG. 2 shows an exemplary embodiment of a computing device for visualizing interactions in an XR scene. The computing device is generally referred to by reference sign 200.

The computing device 200 comprises a first input interface 202-1 configured to receive a first dataset. The first dataset represents an XR scene comprising at least a technical device. The technical device may, e.g., comprise a medical device, in particular a medical imaging device, and more particularly an MRI scanner.

The computing device 200 further comprises a second input interface 202-2 configured to receive, from a set of optical sensors, detected optical sensor data of a user as a second dataset. The optical sensor data (and/or the second dataset) are detected while the user is interacting in a room with the XR scene. The XR scene is displayed to the user on a XR headset or HMD. The set of optical sensors comprises at least one optical sensor at a fixed (and/or predetermined) location relative to the room.

The first input interface 202-1 and the second input interface 202-2 may be comprised in a joint input interface 202.

The computing device 200 still further comprises a computing unit 206 configured to fuse the first dataset and the second dataset for generating a third dataset.

Optionally, the computing device 200 comprises a memory 208. The memory 208 may be configured for storing a fusing algorithm (also: fusion algorithm).

Further optionally, the computing device 200 comprises an output interface 204. The input interfaces 202-1; 202-2; 202 and the output interface 204 may be comprised in an input-and-output interface 210.

The computing device 200 may be comprised in a system, which further comprises one or more XR headsets or HMDs, a set of optical sensors, and optionally the room. The location of at least one optical sensor may be fixed (and/or predetermined) relative to the room.

The computing device 200, e.g., as part of the system, may be configured for executing the method 100.

The present invention can be employed for enabling (and/or improving) virtual usability engineering, e.g., via workflow analysis in fused depth-images of operating a technical device. The technical device may in particular comprise a medical device. The operating of the technical device may, e.g., comprise a virtual MRI examination.

The operating of the technical device according to embodiments of the present invention may comprise using Deep-Learning (DL) methods and augmented reality (AR) or extended reality (XR) techniques.

Digitalization and related space-saving equipment, e.g., RGB-D cameras, and/or sensors built into cellphones (also denoted as mobile phones and/or smartphones), as well as mixed-reality, virtual reality (VR), augmented reality (AR) and extended reality (XR) tools, such as headsets and related displays (e.g., HMDs), and applications have rapidly evolved over the past years.

Digitalization is influencing the technical device industry (including medical device, and particularly medical imaging device, development) significantly. One customer (e.g., a clinic, dentist's surgery, medical office, and/or any association of the former) may, e.g., request a fully autonomous scanner (also denoted as medical imaging device) which is aware of its environment (e.g., by knowing and/or understanding who is using and/or operating the scanner, and/or by knowing and/or understanding which patient interaction and/or preparation is performed) and which can support the user situation specifically (e.g., via mixed-reality techniques).

A user of a technical device may also be denoted as (in particular human) operator of the technical device, e.g., of the medical device, and/or of the scanner. Any medical imaging device may be denoted as scanner.

Today, there is no holistic solution to the described problems of conventional product (e.g., technical device) development, as there are multiple challenges (e.g., usability- and/or requirement engineering, and/or data-collection and/or data-generation) within product development. By the inventive technique, these at least two separate problems and/or topics can be perfectly combined into one approach according to computer graphics techniques, e.g., by combining the fields of CGI (Computer Generated Images, and/or Visualization) and Computer Vision (Scene Understanding, and/or Segmentation).

For usability-engineering, separate methods have been developed to record the user's behavior when working with a functional prototype and/or software module, e.g., by counting the clicks of the user, by eye tracking to detect which are the "hot spots", which parts of the UI (and/or GUI) gets most of the user's attention and might be improved. According to the inventive technique, all of these aspects can be combined into a fully functional "Virtual Usability Lab" using AR technologies.

AR applications are hardly (and/or seldom) used during usability-/requirement engineering. Instead, AR is conventionally used (if used at all) to purely visualize static product concepts to a customer with only limited ways of interaction (e.g., only scaling and/or moving of objects). There is no fully functional AR based prototype, covering the whole workflow (e.g., comprising hardware and software) for any (e.g., medical imaging and/or treatment) modality.

First uses of AR, which are, not directly usability- and/or requirement engineering related, provide some combination of CGI and computer vision (also denoted as visualization) methods, e.g., the so called "Holoportation" by Microsoft Research.

Holoportation aims for connecting people over long distances. E.g., both users and/or operators (in the case of two users) wear AR headsets (e.g., for CGI and/or visualization) and interact in a dedicated room (e.g., the same virtual room, and/or one green screen studio per user) equipped with multiple depth cameras (e.g., RGB-D cameras) generating a color-coded, 3D depth map of the room, including the operators and/or users.

From the one or more 3D depth maps, an algorithm may segment and/or isolate the operator A (Computer Vision) and display a color-coded 3D visualization in the AR scene of operator B. The visualization may comprise a projection as a color-coded point cloud.

As both operators, A and B, use the same equipment according to some embodiment, they may see and/or meet each other virtually in the same AR environment (and/or the same virtual room). The idea, e.g., of extensions of Holoportation, goes far beyond what technologies such as Microsoft Mesh can do today and also requires dedicated equipment, but may provide a promising, new way how to fuse real and virtual environments.

None of the conventional ideas, in particular neither Holoportation nor Microsoft Mesh, is used in the field of usability- and/or requirement engineering. Moreover, the conventional technologies (e.g., including Holoportation, and/or Microsoft Mesh) suffer from one very important point, namely the true (also correct, and/or faithful) registration between real (e.g., the room the operator and/or user is in) and the virtual world (e.g., the scene as displayed in the AR device). However, the real (and/or correct, and/or faithful) registration is very important when using the data, e.g., to generate training data for a scene analysis and/or for machine Learning (ML), in particular according to embodiments of the present invention.

Conventional "projections" are only additional AR scene objects which can be moved and rotated freely. By contrast, according to the inventive technique, the AR scene contains an interaction scheme so that the user (also denoted as operator) can trigger different actions (e.g., table movement, in particular patient table movement) according to a user input and/or so that the user can operate a virtual UI, in particular a virtual GUI (e.g., a touch panel) to mimic the real-world workflow and timing. E.g., the operator may need to position a patient correctly (e.g., relative to a technical device) and enter the necessary data into an operating console of the technical device.

Self-driving cars are an example for autonomous, environment aware systems (and/or technical devices), which use real-time scene analysis, are aware, e.g., of street environment, other cars, and/or traffic lights, and decide autonomously, e.g., when to change direction, and/or when to brake. To achieve this level of automation, a massive amount of training data for all the different algorithms is conventionally needed. Data always has been an asset for autonomous cars and is also one success factor of the company Tesla as they were the first truly entering this market and collecting new real-world training data with every new car they sell.

Especially in the fields of autonomous driving and advanced robotics, the amount of training data is still a demanding topic. Therefore, companies like, e.g., NVIDIA have developed dedicated simulation frameworks (e.g., NVIDIA Isaac Sim platform for robotics, https://developer.nvidia.com/isaac-sim, and/or NVIDI Drive Sim platform for autonomous driving, https://blogs.nvidia.com/blog/2021/11/09/drive-sim-replicator-synthetic-data-generation/?ncid=soyout-833884-vt03 #cid=gtcnov21_so-yout_en-us) especially for autonomous driving and robotics. These platforms allow for simulating real world situations (e.g., different light setting and/or weather, and/or challenging environments) and generating training data for ML Algorithms using, e.g., reinforcement- and/or transfer learning. When an ML algorithm is trained with enough simulated and/or synthetic data, there is a significantly lower demand for real-world data (e.g., corresponding to transfer learning) than if the algorithm was trained on solely real-world data. Big car vendors and/or robot vendors conventionally use these kind of simulation frameworks or even have developed their own.

The new ways of generating synthetic and/or simulated training and test data for ML based algorithms is fascinating and truly a game-changer in this exiting field. Nevertheless, the frameworks conventionally strongly rely on simulating and/or modeling the environment and not on the potential user interaction (e.g., besides people walking across the street), as the human behavior is conventionally considered too hard to model. But with these limitations, the conventional frameworks cannot be used for generating synthetic test data for an autonomous MRI scanner, which needs to understand how the user is interacting with the scene (e.g., also including the patient model).

The inventive technique uses a fully interactive and functional AR (and/or XR) framework in which new product designs, customer workflows, and/or especially the interaction between software and hardware can be explored and/or presented to the customer. The inventive technique uses advanced sensor data (e.g., a 3D depth camera data, in particular an RGB-D camera) to record the user interacting with the virtual AR (and/or XR) scene. Alternatively or in addition, the inventive technique is capable of accurate registration and/or fusion of, e.g., XR scene and optical sensor, datasets (e.g., as 5D point clouds). Further alternatively or in addition, the inventive framework can be used to generate synthetic depth camera images from any arbitrary angle within the (e.g., XR) scene using the recorded 5D point cloud data. The data, and/or datasets, can be further augmented to increase the amount of generated test data and/or be used for the design and/or training of ML based algorithms for scene understanding and/or analysis.

By the inventive technique, a "Virtual Usability Lab" is developed, in which customers can experience functional product concepts at a very early development stage, while their interactions with the virtual (e.g., XR) scene may be recorded and analyzed in real time. The Virtual Usability Lab can serve at least two purposes. Firstly, getting early customer feedback in the development process, e.g., of the technical device. Secondly, generated synthetic training data for ML algorithms (e.g., for scene understanding and/or analysis) can be applied to real-world training data (e.g., once a system, and/or technical device, is developed and installed) via ML methods, e.g., comprising transfer learning.

Applications of the inventive technique comprise integration of AR (and/or XR) into the usability- and/or requirement engineering process by allowing for very early discussion of fully interactive, functional (e.g., in view of hardware and/or software) virtual prototypes with the customer. Alternatively or addition, synthetic test data (and/or test datasets) can be generated for scene understanding ML algorithms. Further alternatively or in addition, scene and/or workflow analysis (e.g., by applying the trained algorithms to the actual scene) is enabled (and/or allowed for). Alternatively or in addition, all interactions of the user with the virtual (e.g., XR) scene may be recorded and/or tracked, and/or analyzed, e.g., to find potential bottlenecks in the human operator workflow (also denoted as user workflow or customer workflow). Alternatively or in addition, techniques such as eye-tracking (e.g., supported by the MS Hololens) may be used as (e.g., additional) sensor data (and/or observation data) for advanced (e.g., real) scene analysis.

In the following, an exemplary embodiment is described.

In a first step (step 1), a visualization of an XR (and/or AR) scene is provided. A fully interactive and functional AR (and/or XR) scene may be implemented using the Microsoft Hololens2 (as an example of an XR headset or HMD) for an MRI examination including a magnet and/or field generation unit (FGU), control room and/or examination room, patient table, patient model, coil, patient data display (PDD) and/or console with interactive GUI.

E.g., as the Microsoft Hololens (as XR headset or HMD) supports hand tracking with its build-in depth cameras, the user may freely interact with the (e.g., XR) scene, e.g., by clicking on the virtual GUI, select the patient to be examined, indication, and/or scan region. The clicking on the virtual GUI may also be denoted as input on a display (e.g., a patient data display, PDD) of the technical device (in particular the medical device) in XR, and/or as input on the GUI of a virtual operating console. Thereby, the real-world behavior of the GUI of a technical device, in particular a medical scanner and/or an operating console, may be mimicked.

The (e.g., XR) scene may implement the complete workflow. E.g., the user may grab objects (e.g., equipment of the MRI scanner, in particular a coil) and place them onto the patient model, position the patient and move the patient table into the isocenter of the MRI scanner by using functional buttons on the (in particular) MRI scanner.

The AR (and/or XR) scene is generated as realistically as possible, covering all necessary aspects so that the simulated and/or reconstructed training images at the end (e.g., see Step 5 below) are as realistic as possible. For the AR (and/or XR) scenes, the Photon Network technology (e.g., according to https://www.photonengine.com/pun) may be used, allowing multiple users to enter and/or interact with the same AR (and/or XR) Scene.

Figure 3:
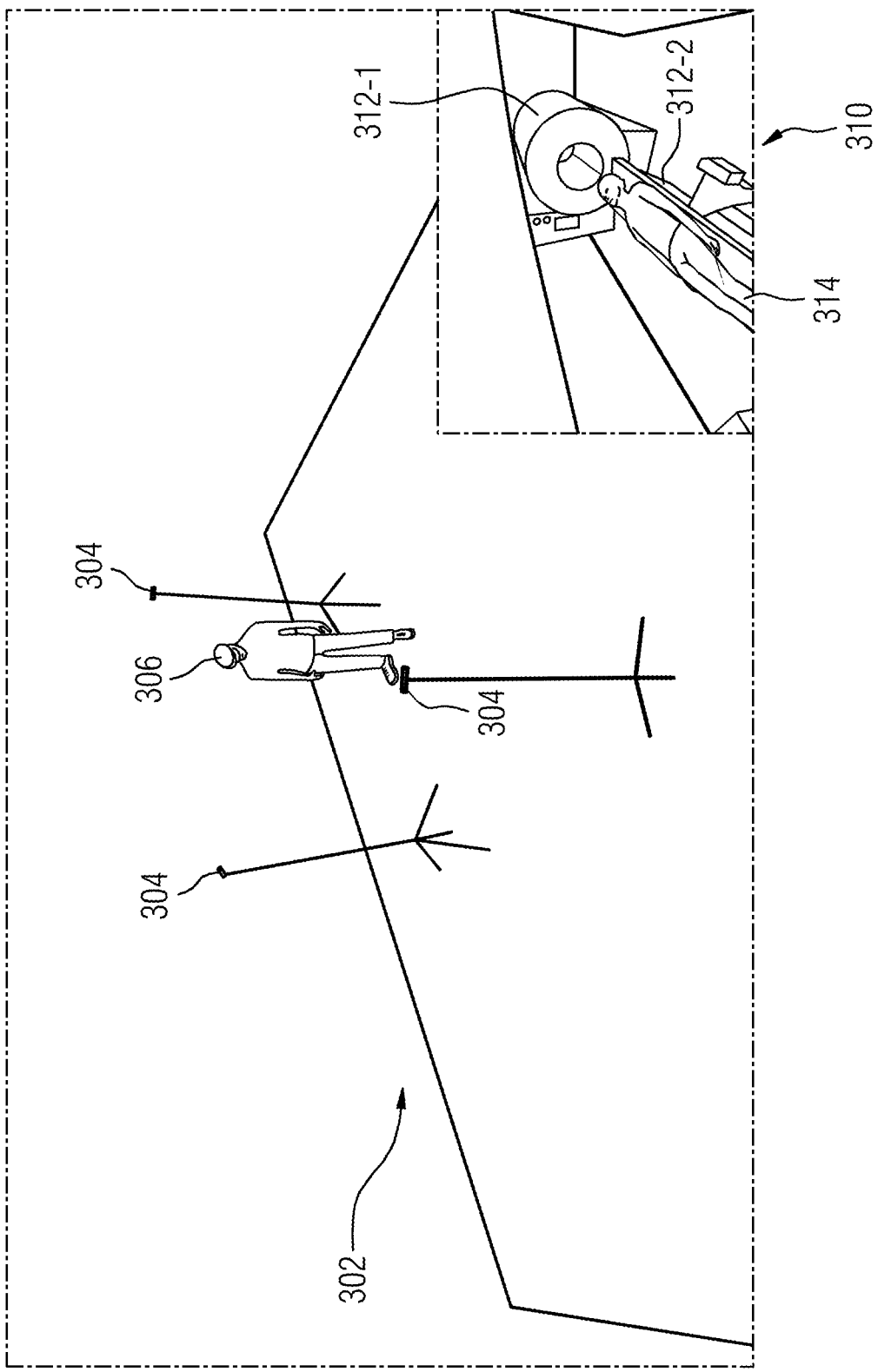
FIG. 3 shows an example of a user located in a room with three optical sensors, as well as inset the XR scene provided to the user on a HMD or XR headset.

FIG. 3 shows the basic set-up. The operator 306 (e.g., wearing the Microsoft Hololens 2 as XR headset or HMD) is in a room 302, and/or an arbitrary office space, and is recorded by three optical sensors 304, in particular three RGB-D cameras (e.g., recording RGB and depth information of the scene). By having three optical sensors, e.g., three cameras, the operator can be covered from different angles in order to calculate a completely color-coded 3D point cloud of the operator 306.

The inserted drawing in the lower right corner of FIG. 3 shows the view through the operator's 306 Hololens. The XR (and/or AR) scene 310 in FIG. 3 comprises an MRI scanner 312-1 with a patient table 312-2, on which a virtual patient 314 is situated. The MRI scanner 312-1 may be an exemplary embodiment of the technical device. The patient table 312-2 may be viewed as equipment of the MRI scanner 312-1. Alternatively or in addition, the patient table 312-2 may be viewed as a further technical device.

The operator 306 is recorded by each of the three depth cameras 304 in FIG. 3. The room 302 may comprise an arbitrary office space, e.g., having at least some empty floor area on which the operator 306 may move freely. Alternatively or in addition, the room 302, as exemplified in FIG. 3 does not include any physical magnet, and/or components of the technical device (e.g., the MRI scanner), and/or equipment of the technical device.

Based on the depth images of the cameras 304, a, e.g., color-coded, surface of the operator 306 may be reconstructed.

Figure 4:
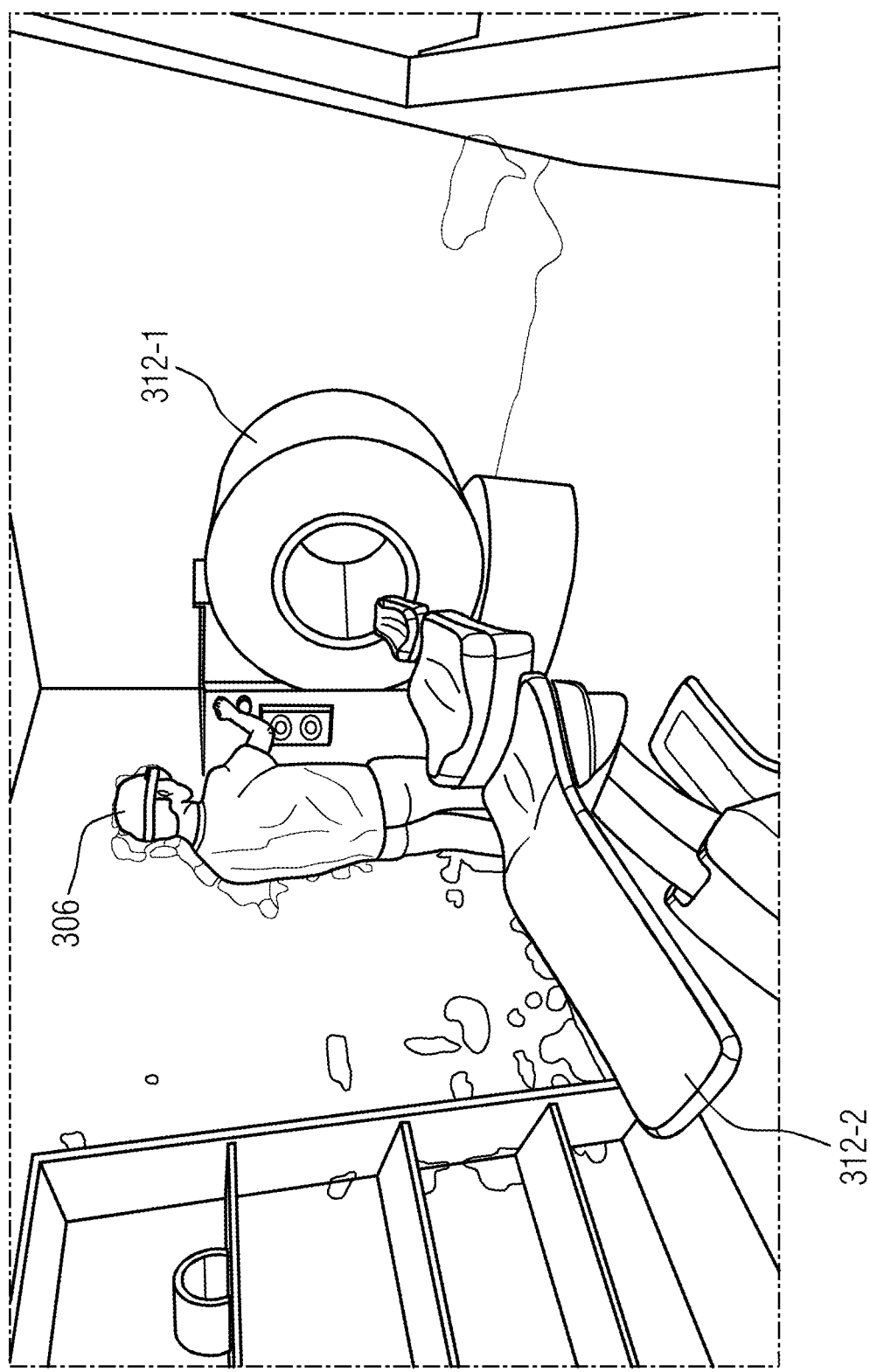
FIG. 4 shows an example of a fused scene comprising the user detected by the optical sensors of FIG. 3 as well as the XR scene as shown inset in FIG. 3.

FIG. 4 shows an example of an image of a fused third dataset comprising the reconstructed operator 306 and the MRI scanner 312-1 as well as the patient table 312-2, e.g., as comprised in the XR (and/or AR) scene 310 in the lower right corner of FIG. 3.

According to the inventive technique, the 3D depth data of the operator 306 are fused with the 3D surface data of the virtual scene 310. FIG. 4 shows the final result, where one can see the operator 306 (as color-coded point cloud) fused with the virtual scene data as presented in the MS Hololens to the operator 306.

FIG. 4 is an example of a synthetic image (in particular comprised in the third dataset generated by suing in the step S110 of the method 100), as this kind of image cannot be detected (and/or recorded) with any optical sensor (e.g., a camera, in particular a depth camera). The synthetic image of FIG. 4 can only be obtained by fusing real and virtual world data, e.g., comprised in the second dataset and in the first dataset, respectively.

Figure 5:
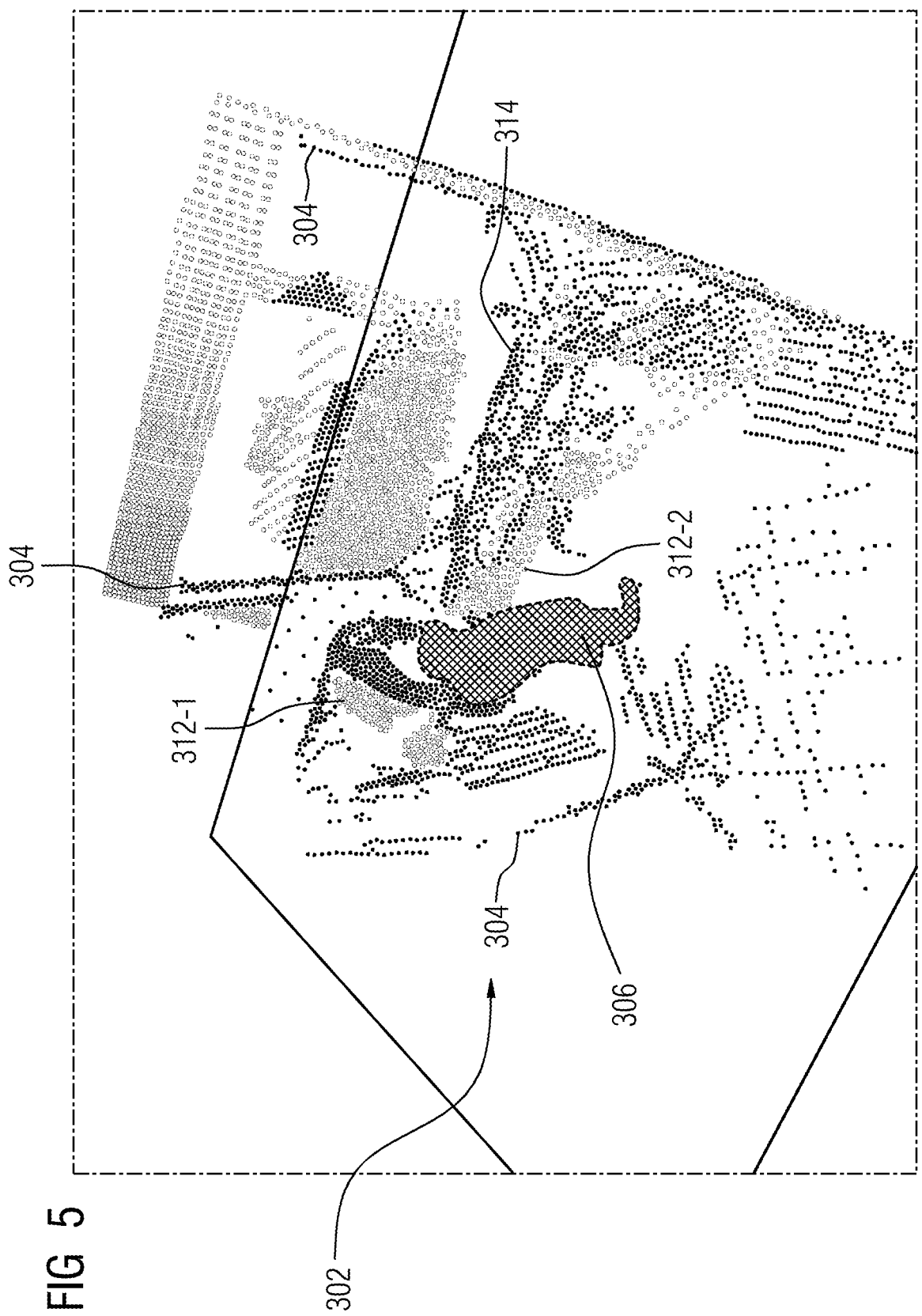
FIG. 5 shows an example of a point-cloud representing the fused scene with color information displayed per point.

An example of a point cloud of the third dataset as a fusion of the first dataset and the second dataset displayed in FIG. 5.

In FIG. 5, the user (also denoted as operator) 306 of an MRI scanner 312-2 is shown in a first (e.g., checkered) style. The remaining (in particular XR) scene (e.g., comprising the MRI scanner 312-1, patient table 312-2 with patient 314 and optical sensors 304 mounted on stands) is shown as points of different shade of gray, or different shade of color. For illustrative purposes, in FIG. 5, light shades are denoted by empty circles, and dark shades are denoted by filled circles.

The inventive technique is powerful because it is capable of modeling, and/or displaying, any kind of user interaction of the operator 306 with the AR (and/or XR) scene, in particular with the technical device (e.g., with the MRI scanner 312-1, and/or the patient table 312-2).

Advantageously, with the inventive technique, all data are available as 5D datasets (e.g., comprising three spatial coordinates, a time-like coordinate, and a color; briefly: x, y, z, time, color). E.g., any one of the first dataset, the second dataset and the third dataset may comprise a 5D dataset. Any one of the datasets may comprise a fusion of partial datasets. E.g., the second dataset comprising optical sensor data may be obtained by fusing a plurality of optical sensor data, each of the optical sensor data corresponding to a different one of the optical sensors. Alternatively or in addition, the second dataset may comprise motion sensor data fused with the optical sensor data from the at least one optical sensor, in particular the at least one optical sensor at a fixed location relative to the room.

The (in particular full) 5D dataset cannot be shown in an (e.g., a single instantaneous) image. Alternatively or in addition, the 5D datasets may be viewed from any arbitrary angle of the scene (e.g., comprising the XR scene). Further alternatively or in addition, different kinds of visualizations may be calculated (e.g., synthetic depth images from any arbitrary angle).

Alternatively or in addition, an analysis (e.g., of the full 5D dataset) may be performed. The analysis can increase the amount of available test datasets for ML algorithms for scene understanding, e.g., by a multiplicative factor. The multiplicative factor may be at least 100, in particular at least 1000 or higher. Alternatively or in addition, different angles and/or different optical sensor (e.g., camera) positions may be comprised in the increased available test datasets.

In a second step (step 2), a registration and/or calibration may be performed. By the registration and/or calibration, a correct (and/or accurate) overlay of the XR (and/or AR) scene with the real-world (in particular optical) sensor data may be enabled.

In order to achieve a high grade of registration quality, a dedicated registration and/or calibration routine may be implemented in the method 100.

Figure 6A:
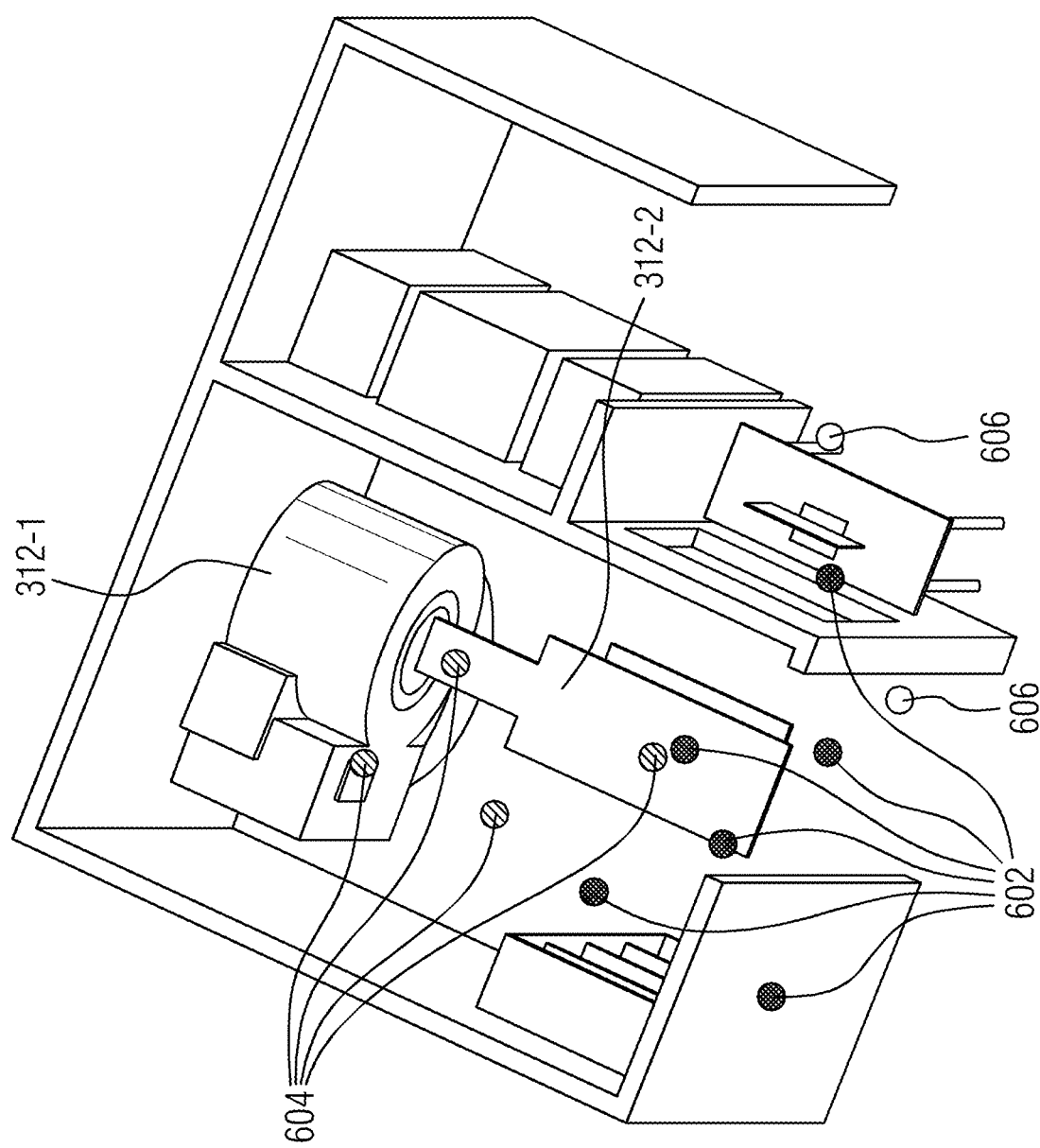
FIGS. 6A and 6B show a registration process by moving real, physical spheres on top of displayed virtual spheres of the XR scene.

In order to register the (in particular optical) sensor data (also denoted as the real world) and the XR (and/or AR) scene (also denoted as the virtual world), a real, physical sphere 602, which may be mounted on a (e.g., simple) camera stand and/or may be freely be moved around in the room, may be used as registration object, as exemplified for a plurality of registration objects in FIG. 6A.

In a dedicated registration step (e.g., in an AR, and/or XR, application), virtual spheres 604 (as, in particular displayed, virtual registration objects) may be displayed at different positions (and/or locations) in the AR (and/or XR) scene (and/or in the virtual room). The virtual spheres 604 may be displayed to the user (and/or operator) 306 by a HMD or XR headset, e.g., via the MS Hololens2.

The user (and/or operator) 306 may be requested to move, e.g., a (e.g., a single one, or one out of the set) real, physical sphere 602 to one position of a (e.g., displayed) virtual sphere 604 in the AR (and/or XR) scene. The user (and/or operator) 306 may be instructed to move the real, physical sphere 602 to a predetermined position (and/or location) of a (e.g., displayed) virtual sphere 604, e.g., according to a predetermined ordering of a set of (e.g., displayed) virtual spheres 604.

According to one embodiment, a single virtual sphere 604 may be displayed at an instant in time of the registration step.

According to another embodiment, at least two (e.g., a set of) virtual spheres 604 may be displayed simultaneously during the registration step.

Figure 6B:
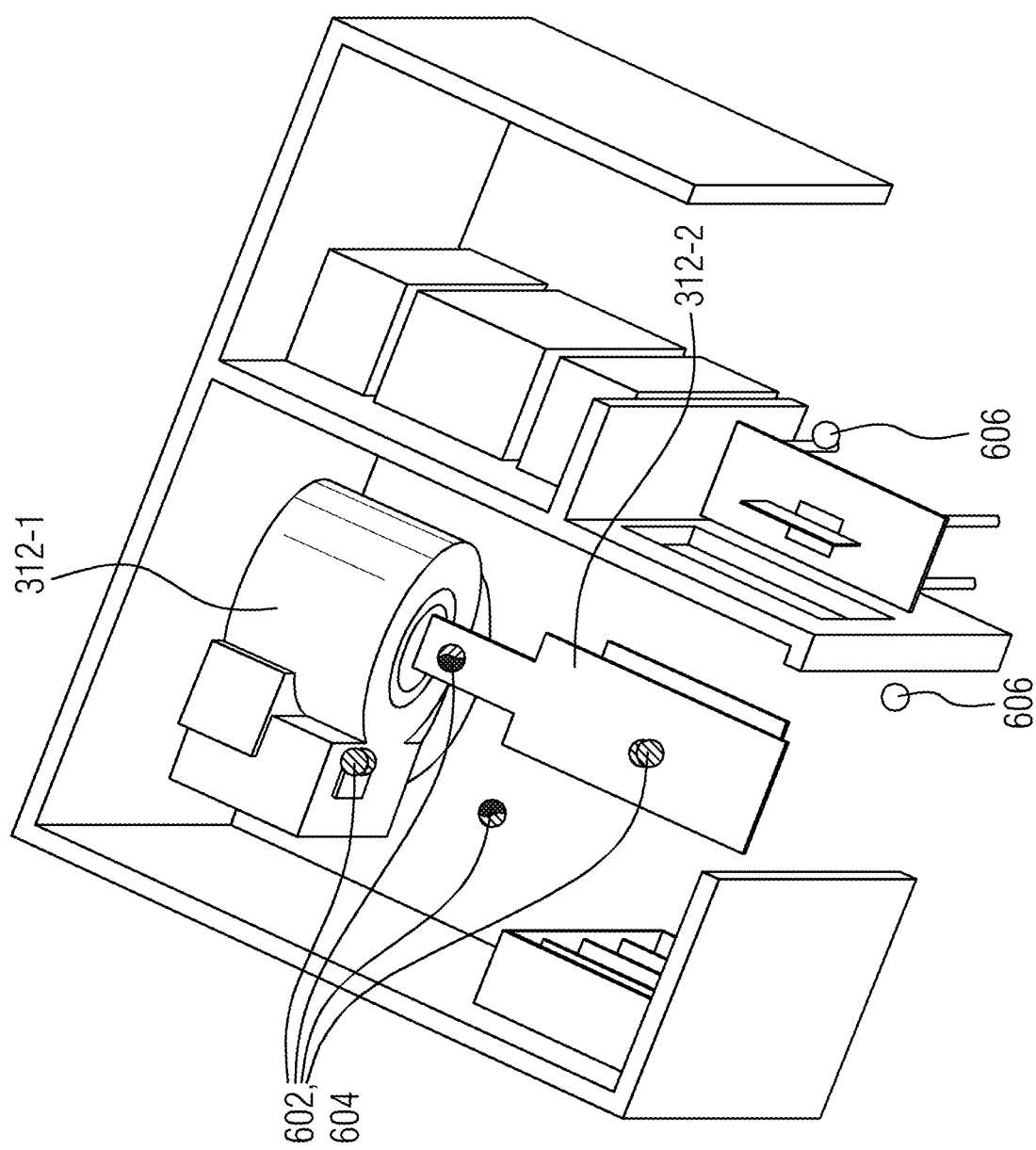

FIG. 6B shows how the user (and/or operator) 306 moved the real, physical spheres 602 to the positions of the displayed virtual spheres 604. The real sphere 602 is seen overlayed by the virtual sphere 604, e.g., in the HMD or XR headset, in particular in the MS Hololens.

In FIGS. 6A and 6B, more than one user (and/or operator) may be present. E.g., two different users (and/or operators) may be simultaneously present at locations denoted by reference sign 606. Any one of the users (and/or operators) may be requested to move the real, physical spheres 602. Alternatively or in addition, the registration procedure may comprise a synchronization of the views of the different users (and/or operators). The synchronization may, e.g., performed using a Photon Network (and/or PUN).

The real, physical spheres 602 may have one color, e.g., green. The displayed virtual spheres 604 may have another color, which differs from the color of the real, physical spheres 604. E.g., the virtual spheres 604 may be displayed in the color orange.

The optical sensors may in particular comprise RGBD cameras.

From the RGB images of the available RGBD cameras (i.e., color image), a real, physical sphere 602 having the one color may be detected by computer vision methods, e.g., shape detection and color information. Alternatively or in addition, from the depth images of the same available RGBD cameras, the 3D coordinates of the real, physical sphere 602 with respect to the different cameras may be determined (e.g., calculated). E.g., a location (and/or position) of the center (e.g., the center of mass) of the real, physical sphere 602 may be determined.

Alternatively or in addition, a location (and/or position) of the outer shell of the real, physical sphere 602 may be determined.

The real, physical sphere 602 may have a diameter in the range of 50 mm to 200 mm, e.g., of 120 mm. The center (e.g., the center of mass) of the real, physical sphere 602 may be located at half the diameter into the interior of the sphere 602 from its outer shell. Alternatively or in addition, the outer shell of the real, physical sphere 602 may be located at half the diameter radially outwards from the center (e.g., the center of mass) of the real, physical sphere 602.

The registration procedure may be repeated, e.g., according to a predetermined ordering, for all displayed virtual spheres 604 in the AR (and/or XR) scene.

A transformation matrix may be determined (e.g., calculated) to correct the transform of the optical sensors (e.g., cameras) in the AR (and/or XR) scene matching the real world data and virtual world data.

E.g., for each optical sensor, in particular camera, the position of the real, physical spheres in global coordinates of a computer vision system (e.g., Unity) scene may be stored in a matrix A and the position of a displayed virtual sphere may be stored in a matrix B:

$$A_i = \begin{bmatrix} \hat{x}_{i,1} & \hat{y}_{i,1} & \hat{z}_{i,1} \\ \ldots & \ldots & \ldots \\ \hat{x}_{i,4} & \hat{y}_{i,4} & \hat{z}_{i,4} \end{bmatrix}, i = 1, 2, B = \begin{bmatrix} x_1 & y_1 & z_1 \\ \ldots & \ldots & \ldots \\ x_4 & y_4 & z_4 \end{bmatrix}.$$

Herein, i=1,2 denotes an exemplary numbering of optical sensors, in particular two cameras 304. The second index 1,2,3,4 of the entries of the matrix Ai as well as the index 1,2,3,4 of the matrix B denotes the numbering of four physical spheres 602.

The matrices Ai and B may be centered by subtracting a centroid. For simplicity of the presentation, the index i of Ai counting the optical sensor, in particular camera 304, is suppressed in the following.

$$A_{center}=A-C_A, B_{center}=B-C_B.$$

From the centered matrices Acenter and Bcenter, a covariance matrix may be computed:

$$M_{Cov}=B_{center} \cdot A_{center}^T.$$

A singular value decomposition (SVD) may be applied to the covariance matrix:

$$U \cdot S \cdot V^T = SVD(M_{Cov}),$$

with transformation matrices U and V and singular value decomposition (SVD) of the covariance matrix MCov.

From this, a rotation of the points of the matrix A may be determined:

$$R=U \cdot V^T.$$

Translations may be computed for each camera and its positions from:

$$t=C_B-R \cdot C_A.$$

The centering of matrices, computing of the covariance matrix, computing of the SVD, as well as the resulting rotation R and translation t are performed each of a plurality of optical sensors, in particular cameras 304, separately. Alternatively or in addition, the index i carries through the computation (e.g., Ai,center⇒Mi,Cov⇒Ui, Vi⇒Ri, ti).

A calibration of each of the optical sensors may comprise the registration of the registration objects, in particular, the registration spheres. Alternatively or in addition, a calibration of each of the optical sensors may comprise, based in the registration step, selecting (and/or adjusting) intrinsic camera parameters, and/or extrinsic camera parameters.

The visualization in FIG. 4 may use the registration and/or calibration according to the second step (step 2). The user (and/or operator) 306 may, e.g., freely, move around in the room while observing (and/or) watching the AR (and/or XR) scene in the HMD or XR headset, in particular the MS Hololens. The user's (and/or operator's) 306 position in the synthetic (and/or fused) image (e.g., according to the third dataset) may be updated in real-time accordingly to the registration and/or calibration, and according to depth scene data (e.g., if the user, and/or operator, 306 stands in front, and/or behind the patient table and/or patient chair).

The advanced visualization according to the inventive technique, which takes the real-world data into account according to the second step (step 2), allows for real-time displaying of the user (and/or operator 306) interaction with the virtual (e.g., XR) scene for observers without a HMD or XR headset, e.g., not wearing the MS Hololens. Conventionally, only users (and/or observers) within the (e.g., XR) scene (e.g., using a HMD or XR headset, in particular wearing the MS Hololens) can see the interaction of the other users in the same (e.g., XR) scene.

The registration (and/or calibration) method of the second step (sept 2) may be extended to not only track and/or register real-world spheres (e.g., as used in FIGS. 6A and 6B), but may also track other real-world objects such as robotics and/or monitor arms, and/or (e.g., in-room) equipment of the technical device, in particular the medical device (e.g., the MRI scanner 312-1) with computer vision methods. The computer vision methods may, e.g., comprise object detection, shape recognition, and/or ML based detectors.

With the extension of the registration (and/or calibration) method, e.g., overlaying new concepts for robotic devices on-top of the conventional holder structures may be enabled. Alternatively or in addition, new ways of interacting with robotic devices and/or monitors may be introduced, e.g., with the built-in gesture detection and/or hand tracking capabilities of the HMD or XR headset, e.g., extending the Microsoft Hololens 2. Alternatively or in addition, AR and/or XR may be extended, e.g., enabling early concept discussions and/or usability engineering for surgical procedures.

In a third step (step 3), point-clouds are generated, e.g., virtual point-clouds for the first dataset, and/or point-clouds for the second dataset.

FIGS. 7A to 7G show an example of generating a virtual point-cloud as the third dataset.

Figure 7A:
Figure 7B:
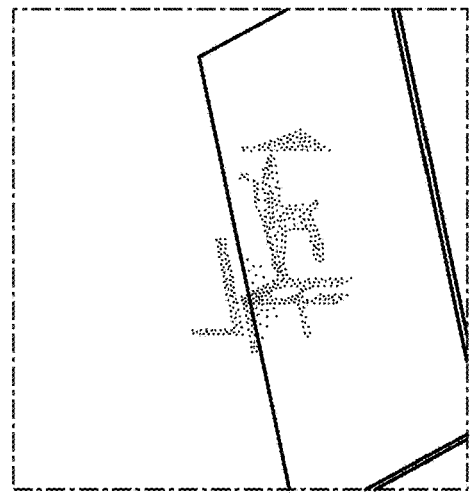
Figure 7C:
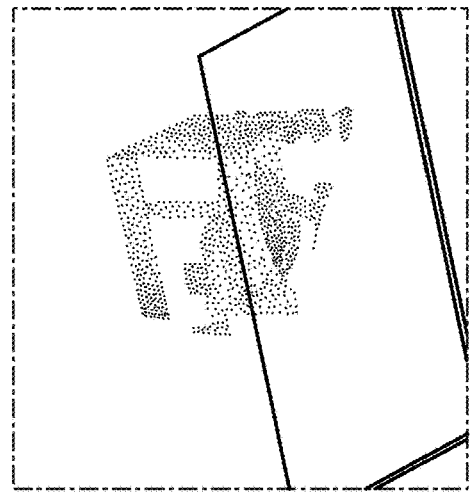

In FIG. 7C as the first dataset, two virtual point-clouds from FIGS. 7A and 7B are fused, which correspond to different angles of view (e.g., corresponding to different angles of the optical sensors, in particular depth cameras).

In FIG. 7F as the second dataset, two point-clouds from FIGS. 7D and 7E are fused, which correspond to different angles of view of the optical sensor data (e.g., from the optical sensors, in particular RGBD cameras, 304).

FIG. 7G shows the third dataset as a virtual point-cloud obtained from fusing of the virtual point-cloud of the first dataset of FIG. 7C with the point-cloud of the second dataset of FIG. 7F.

The inventive technique mainly builds upon using 3D point clouds as (e.g., XR) scene representation, e.g., per instant in time. The 3D point clouds may be generated from 3D surface data and/or computer-aided design (CAD) data of the AR (and/or XR scene (e.g., comprising a magnet and/or FGU of an MRI scanner, a patient table, and/or a patient model).

A patient model may be, or may comprise, a computer model comprising a surface mesh and applied textures (e.g., color images, overlayed onto the mesh data) to make the patient model look like a real patient (in particular a human). Similar models may be used in computer games or in 3D renderings for product presentations. A (e.g., comprehensive) database may be generated. Animations may be applied to the patient models to make the XR scene (also denoted as: act) more realistic, e.g., with the patient walking into the MRI room, and/or sitting on a patient table (and/or patient bed). Alternatively or in addition, real movement data of real patients may be recorded and/or applied the animation files of the patient models. E.g., a synthetically generated animation of a patient model may be modified based on the recorded real movement data.

To make the (e.g., XR) scene, and/or a patient movement, even more realistic, random movements may be added, e.g., to simulate a freezing patient and/or movement during patient preparation (e.g., when applying coils to a patient for an MRI scan).

The patient model may including animations (e.g., movements of a human patient) also be denoted as dynamic patient model.

By the (e.g., dynamic) patient models, a realism of the generated (e.g., XR) scenes can be improved. Alternatively or in addition, the (e.g., dynamic) patient models can positively influence (e.g., augment) the amount of available training data.

The generating of the point-clouds of the first dataset, and/or of the second dataset, can be done within a development framework for computer vision (e.g., Unity) by simple, e.g., scan-line algorithms to trace the surface of the objects within the scene. E.g., FIG. 7C shows the generated point-cloud data of the AR (and/or XR) scene. Alternatively or in addition, e.g., FIG. 7F shows the generated point-cloud data of the detected optical sensor data.

In a fourth step (step 4), the (e.g., virtual) point-clouds of the first dataset are fused with the point-clouds of the optical sensor data, e.g., depth camera data, and/or of the second dataset.

The virtual (e.g., AR, and/or XR, scene) and real (operator, and/or optical sensor data, in particular depth camera) 3D point cloud data sets corresponding to the first dataset and the second dataset, respectively, are fused using the registration and/or calibration determined (e.g., calculated) in the second step (e.g., step 2). FIG. 7G shows the result of the fusing and/or combining the point-clouds recorded from the depth cameras (e.g., as displayed in FIG. 7F) and the ones as determined (e.g., calculated) from the virtual point-clouds of the XR (and/or AR) scene in the third step (step 3), e.g., as displayed in FIG. 7C.

It is noted that even if the references images are only shown in two-dimensions (2D) in FIG. 5 as well as FIGS. 7A to 7D, the fused point-cloud representation (e.g., as determined, and/or calculated, in the fourth step, step 4) is a (e.g., true) 5D dataset (e.g., comprising spatial and time-like coordinates as well as color; briefly: x, y, z, time, color).

An example of the of fusing the point-clouds, including taking the color information for the operator 306 and/or the AR (and/or XR) scene (e.g., comprising an MRI scanner and a patient on a patient table) into account, is provided by FIG. 5.

In a fifth step (step 5), further determinations, calculations, and/or reconstructions may be performed on the fused third datasets, e.g., the point-clouds comprising a 5D representation with x,y,z,t coordinated and color information per data point, as, e.g., exemplified in FIG. 5. E.g., if the user (and/or operator) 306 grabs an object, and/or equipment, in the scene, e.g., a coil (as an example of equipment of an MRI scanner) and moves the object, the 5D scene representation is updated accordingly.

The 5D scene representation, and/or the 5D data representation, allows for multiple ways for training data generation for ML, and/or for scene understanding, and/or analysis, algorithms.

Reconstructions may comprise a variety of different virtual, synthetic depth cameras from any arbitrary position, and/or any angle with different camera characteristics. E.g., synthetic depth camera images may be determined (and/or calculated) which a real RGBD camera would see in such a scene, e.g., if the inventive system is operationally installed (in particular, if at least one optical sensor and/or RGBD camera is installed in a room).

Alternatively or in addition, reconstructions may comprise a variety of RGBD images from any arbitrary position, angle, and/or size.

Further alternatively or in addition, reconstructions may comprise a variety of three-dimensional (3D) reconstructions.

The inventive technique in particular applies to a medical device, and more particularly to a medical imaging device (e.g., an MRI scanner 312-1), as the at least one technical device in the XR scene, with which the user (and/or operator) 306 interacts. Alternatively or in addition, the at least one technical device may comprise robotics, and/or an autonomously driving vehicle, with which the user (and/or operator) 306 interacts according to the inventive technique.

The generated data (and/or, e.g., third, datasets) may be augmented, e.g., by animating the patient model, adding arbitrary movement, modifying the operator's 306 pose, and/or change position and/or angle for reconstructed images for ML. By augmenting the data (and/or, e.g., third, datasets), the amount of, e.g., third, datasets available for ML applications may be increased, e.g., by a multiplicative factor. The multiplicative factor may be at least 1000, in particular at least 10000 or higher.

An ML algorithm may be applied to the, e.g., third, datasets in order to generate training and/or test data. Alternatively or in addition a ML based algorithm may be developed for scene understanding and/or analysis.

The ML algorithm, and/or the reconstructions, may comprise a semantic scene segmentation and/or understanding. Alternatively or in addition, the ML algorithm, and/or the reconstructions, may comprise a human pose detection. E.g., the pose of the user (and/or operator) 306 may be detected. Alternatively or in addition, a patient's skeleton, and/or joints may be detected. Further alternatively or in addition, the ML algorithm, and/or the reconstructions, may comprise a pose tracking and/or action prediction, e.g., learning the action the user (and/or operator) 306 is about to perform in the (e.g., XR) scene. Still further alternatively or in addition, the ML algorithm, and/or the reconstructions, may comprise a workflow step detection and/or classification, e.g., for clinical supervision.

The ML based algorithm may be trained using the presented AR (and/or XR) framework and data representation (e.g., comprising the first dataset, second dataset, and/or third dataset).

By the inventive technique, an autonomy of a technical device, in particular a medical device (and more particularly a medical imaging device, e.g., an MRI scanner), and/or its awareness of, and/or interaction with, the environment may be improved. The environment may, e.g., comprise the user (and/or operator) 306. Alternatively or in addition, the environment may comprise a patient to be examined.

FIG. 8 shows two exemplary alternative uses of applying a CycleGAN for image-to-image transfer and subsequently applying a (in particular different from the CycleGAN) neural network, in particular an RfD-Net, for determining a semantic context, when fusing a first dataset 806 representing an XR scene with at least one technical device, in particular a medical device, and a second dataset 808 comprising (in particular optical) sensor data indicative of a user's interaction with the technical device, in particular the medical device.

According to the first alternative 802, the first dataset 806 and the second dataset 808 are fused at reference sign 812 in order to obtain a third dataset 810. The third dataset 810 undergoes image-to-image transfer via the CycleGAN as shown at reference sign 814. The output of the CycleGAN is a modified third dataset 810-1, which is, as shown at reference sign 816, input into a (in particular different from the CycleGAN) neural network, e.g., a RfD-Net. At reference sign 810-2, a further modified third dataset is output comprising a semantic context.

According to the second alternative 804, the first dataset 806 is input, as shown at reference sign 814, into the CycleGAN, to obtain an image-to-image transferred (also denoted as modified) first dataset 806-1. The modified first dataset 806-1 and the second dataset 808 are fused at reference sign 812 to obtain a third dataset 810, which is input, as shown at reference sign 816, into a (in particular different from the CycleGAN) neural network, e.g., a RfD-Net. The output of the neural network, e.g., the RfD-Net, at reference sign 810-2 comprises a modified third dataset with a semantic context.

FIG. 9 shows a detailed example of generating a more realistic (e.g., photorealistic) image from a virtual image, e.g., corresponding to the first dataset, using a CycleGAN.

FIG. 9A shows a depth image of an MRI scanner 312-1 with a patient table 312-2 as an example of a technical device (and/or a combination of two technical devices) as obtained from a real depth camera, e.g., an RGBD camera.

FIG. 9B shows an exemplary generated synthetic depth image, e.g., using a shader in a computer vision system (e.g., Unity), of a scene with similar geometries as in FIG. 9A. At reference sign 902, depth images obtained from a real depth camera, and/or generated synthetic depth images, are used to train a CycleGAN.

FIG. 9C exemplifies the step 814 of applying a Cycle-GAN for image-to-image transfer to the synthetic depth image of FIG. 9B in order to arrive at a modified (e.g., more realistic and/or photorealistic) version of the image, comprising the MRI scanner 312-1 and the patient table 312-2, in FIG. 9D.

Figure 10:
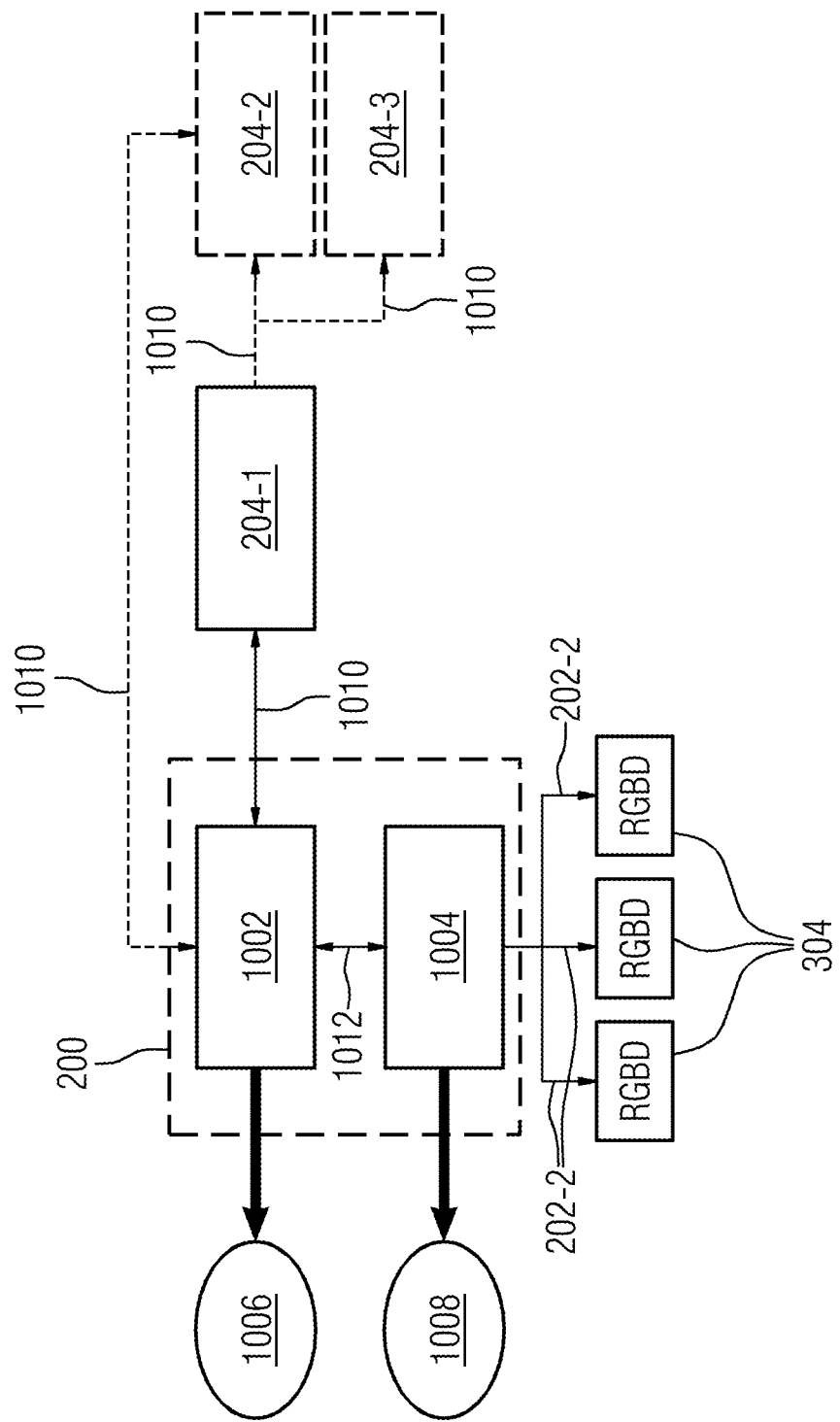
FIG. 10 shows an example of using a photon unity network (PUN) for performing the method of FIG. 1, in particular with multiple users in the same XR scene.

FIG. 10 shows an exemplary embodiment of the workings of a system comprising a computing device 200, a multitude of HMDs and/or XR headsets (e.g., Hololenses) 204-1; 204-2; 204-3 and optical sensors 304.

As depicted as reference sign 1002, the computing device 200 may comprise a computer vision system (e.g., Unity) 1002, which through a TCP Client/Service 1012 connects to a software and/or programming language (e.g., Python) interface 1004, which over the second input interfaces 202-2 connects to the optical sensors 304.

The multitude of HMDs and/or XR headsets (e.g., Hololenses) 204-1; 204-2; 204-3 in FIG. 10 are connected among each other as well as with the computing device 200 through the PUN 1010.

The output of the computer vision system (e.g., Unity) 1002 comprises one or more virtual point clouds 1002.

The output of the software and/or programming language (e.g., Python) interface 1008 comprises one or more real point clouds 1008.

The (e.g., complete) 3D scene (e.g., comprising the third dataset) may be implemented in a computer vision system (e.g., Unity) based on computer-aided design (CAD) models.

By the inventive technique, a development (also denoted as product development) of technical devices, in particular of medical devices (and more particularly medical imaging devices, e.g., of MRI scanners) may be improved, rendered more efficient, and/or accelerated.

Alternatively or in addition, by the inventive technique, synthetic data generation may be improved (e.g., using the third dataset), and/or ML based algorithms and/or automatisms may be improved, and/or developed.

The inventive technique far exceeds the conventional Microsoft Mesh and Holoportation projects as well as the conventional developments in the automotive drive and/or robotics industry (e.g., NVIDIA's simulation frameworks for synthetic data generation for ML based applications) by incorporating the operator's (and/or user's) interactions. Alternatively or in addition, workflow modeling, in particular comprising a medical workflow, may be improved, e.g., in terms of a patient's safety (e.g., by choosing the least invasive examination method, a minimal amount of radiation, and/or a minimum magnetic field strength, and/or by ensuring that an implant, e.g., a cardiac pacemaker, is correctly taken into account) and/or speed of an examination.

The Inventive technique allows for very early customer involvement and/or feedback with a high level of immersion (e.g., via rendering an image of the third dataset, and/or by a user performing virtual tests on the operation of the at least one technical device in the XR scene) during the development of a technical device. Alternatively or in addition, training data for scene understanding and/or analysis for the technical device may already be generated during the development, construction and/or assembly phase of the real, physical technical device. Further alternatively or in addition, the development of novel technical devices may be de-risked. E.g., by virtually monitoring, and/or controlling the operating of a dental MRI scanner under development, it may be ensured that all (e.g., confined) space and operational (e.g., reachability) constraints may be met.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents. Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of present invention or with respect to a particular figure are, wherever applicable, also advantages of other embodiments of the present invention.

What is claimed is:

1. A computer-implemented method for visualizing interactions in an extended reality (XR) scene, the computer-implemented method comprising:
    receiving a first dataset, the first dataset representing the XR scene including at least a technical device;
    displaying the XR scene on an XR headset or a head-mounted display (HMD);
    providing a room for a user, wherein the user wears the XR headset or HMD to interact with the XR scene, wherein the XR scene is displayed on the XR headset or HMD, wherein the room includes a set of optical sensors, and wherein the set of optical sensors includes at least one optical sensor at a fixed location relative to the room;
    detecting, via the set of optical sensors, optical sensor data of the user as a second dataset while the user is interacting in the room with the XR scene, wherein the XR scene is displayed on the XR headset or HMD; and
    fusing the first dataset and the second dataset to generate a third dataset, wherein
        the first dataset, the second dataset and the third dataset include a point cloud, and
        the third dataset includes a fusion of point clouds of the first dataset and the second dataset.

2. The computer-implemented method according to claim 1, wherein the set of optical sensors includes at least one depth camera to provide point cloud data.

3. The computer-implemented method according to claim 1, further comprising:

generating real-time instructions based on the third dataset; and
providing the real-time instructions to the user.

4. The computer-implemented method according to claim 1, wherein the computer-implemented method is used for at least one of product development of the technical device or for controlling the technical device.

5. A non-transitory computer-readable storage medium storing computer-executable instructions that, when executed by a computing device, cause the computing device to perform the computer-implemented method according to claim 1.

6. The computer-implemented method according to claim 2, wherein the at least one depth camera includes an RGBD camera.

7. The computer-implemented method according to claim 1, wherein a trained neural network is used to provide output data based on input data, wherein the input data includes the third dataset and the output data represents a semantic context of the optical sensor data of the user.

8. A computer-implemented method for visualizing interactions in an extended reality (XR) scene, the computer-implemented method comprising:
receiving a first dataset, the first dataset representing the XR scene including at least a technical device;
displaying the XR scene on an XR headset or a head-mounted display (HMD);
providing a room for a user, wherein the user wears the XR headset or HMD to interact with the XR scene, wherein the XR scene is displayed on the XR headset or HMD, wherein the room includes a set of optical sensors, and wherein the set of optical sensors includes at least one optical sensor at a fixed location relative to the room;
detecting, via the set of optical sensors, optical sensor data of the user as a second dataset while the user is interacting in the room with the XR scene, wherein the XR scene is displayed on the XR headset or HMD; and
fusing the first dataset and the second dataset to generate a third dataset, wherein
a trained neural network is used to provide output data based on input data, wherein the input data includes the third dataset and the output data represents a semantic context of the optical sensor data of the user.

9. The computer-implemented method according to claim 8, wherein the trained neural network is trained by providing the input data including the third dataset, which is labeled with content data, wherein the content data represents a semantic context of user interaction.

10. The computer-implemented method according to claim 8, further comprising:
pre-processing the third dataset before being used as the input data for the trained neural network, wherein the pre-processing includes application of an image-to-image transfer learning algorithm to the third dataset.

11. The computer-implemented method according to claim 8, further comprising:
pre-processing the first dataset before fusion with the second dataset, wherein the pre-processing includes application of an image-to-image transfer learning algorithm to the first dataset, wherein the generating of the third dataset includes fusing the pre-processed first dataset and the second dataset.

12. The computer-implemented method according to claim 8, wherein the trained neural network is further configured to receive, as input data, detected optical sensor data of a user interacting with a real-world scene, wherein the real-world scene includes a real-world technical device, wherein the real-world technical device corresponds to the technical device of the XR scene.

13. The computer-implemented method according to claim 11, wherein the fusing includes applying a calibration algorithm, which utilizes at least one registration object deployed in the room.

14. The computer-implemented method according to claim 13, wherein the calibration algorithm uses a set of registration objects, which are provided as real, physical objects in the room and which are provided as displayed virtual objects in the XR scene, wherein for registration purposes, the real, physical objects are moved to match the displayed virtual objects in the XR scene.

15. The computer-implemented method according to claim 14, wherein the real, physical objects include a first set of spheres, and wherein the displayed virtual objects include a second set of spheres.

16. A computing device for visualizing interactions in an extended reality (XR) scene, the computing device comprising:
a first input interface configured to receive a first dataset, the first dataset representing the XR scene including at least a technical device;
a second input interface configured to receive, from a set of optical sensors, detected optical sensor data of a user as a second dataset while the user is interacting in a room with the XR scene, wherein the XR scene is displayed to the user on a XR headset or head-mounted display (HMD), and wherein the set of optical sensors includes at least one optical sensor at a fixed location relative to the room; and
at least one processor configured to fuse the first dataset and the second dataset to generate a third dataset, wherein
the first dataset, the second dataset and the third dataset include a point cloud, and
the third dataset includes a fusion of point clouds of the first dataset and the second dataset.

17. A system for visualizing interactions in an extended reality (XR) scene, the system comprising:
at least one of at least one XR headset or at least one head-mounted display (HMD);
an XR scene generating device configured to generate a first dataset, the first data set representing the XR scene including at least a technical device, wherein the XR scene is to be displayed on the at least one of the at least one XR headset or the at least one HMD;
a set of optical sensors configured to detect optical sensor data of a user as a second dataset, while the user is interacting in a room with the XR scene, the XR scene being displayable on the at least one of the at least one XR headset or the at least one HMD, and wherein the set of optical sensors includes at least one optical sensor at a fixed location relative to the room; and
a computing device configured to execute a fusing algorithm to fuse the first dataset with the second dataset to generate a third dataset, the computing device including
a first input interface configured to receive the first dataset,
a second input interface configured to receive, from the set of optical sensors, the optical sensor data of the user as the second dataset, and at least one processor configured to execute the fuse algorithm to fuse the first dataset with the second dataset to generate the third dataset, wherein
at least one of (i) the at least one XR headset or the at least one HMD, (ii) the computing device, or (ii) the XR scene generating device are connected via a photon unity network (PUN).

18. The system according to claim 17,
wherein the first dataset, the second dataset and the third dataset include a point cloud, and
wherein the third dataset includes a fusion of point clouds of the first dataset and the second dataset.

19. A computing device for visualizing interactions in an extended reality (XR) scene, the computing device comprising:
a first input interface configured to receive a first dataset, the first dataset representing the XR scene including at least a technical device;
a second input interface configured to receive, from a set of optical sensors, detected optical sensor data of a user as a second dataset while the user is interacting in a room with the XR scene, wherein the XR scene is displayed to the user on a XR headset or head-mounted display (HMD), and wherein the set of optical sensors includes at least one optical sensor at a fixed location relative to the room; and
at least one processor configured to fuse the first dataset and the second dataset to generate a third dataset, wherein
a trained neural network is used to provide output data based on input data, wherein the input data includes the third dataset and the output data represents a semantic context of the detected optical sensor data of the user.

* * * * *